(12) United States Patent
Weerakoon et al.

(10) Patent No.: US 12,042,291 B2
(45) Date of Patent: *Jul. 23, 2024

(54) CIRCUITRY TO ASSIST WITH NEURAL SENSING IN AN IMPLANTABLE STIMULATOR DEVICE IN THE PRESENCE OF STIMULATION ARTIFACTS

(71) Applicant: Boston Scientific Neuromodulation Corporation, Valencia, CA (US)

(72) Inventors: Pujitha Weerakoon, Valencia, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,222

(22) Filed: Mar. 16, 2023

(65) Prior Publication Data

US 2023/0218217 A1 Jul. 13, 2023

Related U.S. Application Data

(63) Continuation of application No. 16/821,602, filed on Mar. 17, 2020, now Pat. No. 11,633,138.

(Continued)

(51) Int. Cl.
*A61B 5/00* (2006.01)
*A61B 5/24* (2021.01)
(Continued)

(52) U.S. Cl.
CPC ............... *A61B 5/24* (2021.01); *A61B 5/686* (2013.01); *A61B 5/7217* (2013.01); *A61N 1/05* (2013.01);
(Continued)

(58) Field of Classification Search
CPC . A61B 2562/0209; A61B 5/24; A61B 5/4848; A61B 5/686; A61B 5/7217;
(Continued)

(56) References Cited

U.S. PATENT DOCUMENTS 4,677,986 A 7/1987 Decote, Jr.
5,697,958 A 12/1997 Paul et al.
(Continued)

FOREIGN PATENT DOCUMENTS

EP 1147784 10/2001
WO 2015/077362 5/2015
(Continued)

OTHER PUBLICATIONS

International Search Report and Written Opinion regarding corresponding PCT Application No. PCT/US2020/023182, mailed Jun. 4, 2020.

*Primary Examiner* — Jon Eric C Morales
(74) *Attorney, Agent, or Firm* — Lewis & Reese, PLLC

(57) ABSTRACT

Sense amplifier circuits particularly useful in sensing neural responses in an Implantable Pulse Generator (IPG) are disclosed. The IPG includes a plurality of electrodes, with one selected as a sensing electrode and another selected as a reference to differentially sense the neural response in a manner that subtracts a common mode voltage (e.g., stimulation artifact) from the measurement. The circuits include a differential amplifier which receives the selected electrodes at its inputs, and comparator circuitries to assess each differential amplifier input to determine whether it is of a magnitude that is consistent with the differential amplifier's input requirements. Based on these determinations, an enable signal is generated which informs whether the output of the differential amplifier validly provides the neural response at any point in time. Further, clamping circuits are connected to the differential amplifier inputs to clamp these (Continued)

inputs in magnitude to prevent the differential amplifier from damage.

20 Claims, 11 Drawing Sheets

Related U.S. Application Data

(60) Provisional application No. 62/825,981, filed on Mar. 29, 2019.

(51) Int. Cl.
*A61N 1/05* (2006.01)
*A61N 1/36* (2006.01)
*A61N 1/08* (2006.01)

(52) U.S. Cl.
CPC ..... *A61N 1/36125* (2013.01); *A61N 1/36139* (2013.01); *A61B 2562/0209* (2013.01); *A61N 1/08* (2013.01)

(58) Field of Classification Search
CPC ........ A61B 5/7225; A61N 1/025; A61N 1/05; A61N 1/0553; A61N 1/08; A61N 1/36062; A61N 1/36125; A61N 1/36139
See application file for complete search history.

(56) References Cited

U.S. PATENT DOCUMENTS

| | | |
|---|---|---|
| 5,702,429 A | 12/1997 | King |
| 5,902,236 A | 5/1999 | Iversen |
| 5,902,249 A | 5/1999 | Lyster |
| 5,913,882 A | 6/1999 | King |
| 6,181,969 B1 | 1/2001 | Gord |
| 6,516,227 B1 | 2/2003 | Meadows et al. |
| 7,024,247 B2 | 4/2006 | Gliner et al. |
| 7,424,322 B2 | 9/2008 | Lombardi et al. |
| 7,450,992 B1 | 11/2008 | Cameron |
| 8,255,057 B2 | 8/2012 | Fang et al. |
| 8,335,664 B2 | 12/2012 | Eberle |
| 8,352,030 B2 | 1/2013 | Denison |
| 8,606,362 B2 | 12/2013 | He et al. |
| 8,620,436 B2 | 12/2013 | Parramon et al. |
| 9,044,155 B2 | 6/2015 | Strahl |
| 9,155,892 B2 | 10/2015 | Parker et al. |
| 9,248,274 B2 | 2/2016 | Troosters et al. |
| 9,248,279 B2 | 2/2016 | Chen et al. |
| 9,265,431 B2 | 2/2016 | Hincapie Ordonez et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,403,013 B2 | 8/2016 | Walker et al. |
| 9,409,020 B2 | 8/2016 | Parker |
| 9,526,897 B2 | 12/2016 | Chen et al. |
| 9,533,148 B2 | 1/2017 | Carcieri |
| 9,731,116 B2 | 8/2017 | Chen |
| 9,872,990 B2 | 1/2018 | Parker et al. |
| 9,974,455 B2 | 5/2018 | Parker et al. |
| 10,076,667 B2 | 9/2018 | Kaula et al. |
| 11,633,138 B2 * | 4/2023 | Weerakoon ........ A61N 1/36062 600/377 |
| 2002/0156513 A1 | 10/2002 | Borkan |
| 2005/0246004 A1 | 11/2005 | Cameron et al. |
| 2008/0146894 A1 | 6/2008 | Bulkes et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2014/0194772 A1 | 7/2014 | Single et al. |
| 2014/0236042 A1 | 8/2014 | Parker et al. |
| 2014/0296737 A1 | 10/2014 | Parker et al. |
| 2015/0157861 A1 | 6/2015 | Aghassian |
| 2015/0282725 A1 | 10/2015 | Single |
| 2015/0313487 A1 | 11/2015 | Single et al. |
| 2016/0166164 A1 | 6/2016 | Obradovic et al. |
| 2016/0287126 A1 | 10/2016 | Parker et al. |
| 2016/0287182 A1 | 10/2016 | Single |
| 2017/0042482 A1 | 2/2017 | Gunderson et al. |
| 2017/0049345 A1 | 2/2017 | Single |
| 2017/0071490 A1 | 3/2017 | Parker et al. |
| 2017/0135624 A1 | 5/2017 | Parker |
| 2017/0216587 A1 | 8/2017 | Parker |
| 2017/0296823 A1 | 10/2017 | Hershey et al. |
| 2017/0361101 A1 | 12/2017 | Single |
| 2018/0071527 A1 | 3/2018 | Feldman et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0140831 A1 | 5/2018 | Feldman et al. |
| 2018/0228391 A1 | 8/2018 | Parker et al. |
| 2018/0228547 A1 | 8/2018 | Parker et al. |
| 2018/0256052 A1 | 9/2018 | Parker et al. |
| 2019/0076645 A1 | 3/2019 | Bower et al. |
| 2019/0099602 A1 | 4/2019 | Esteller et al. |
| 2019/0175915 A1 | 6/2019 | Brill et al. |
| 2019/0209844 A1 | 7/2019 | Esteller et al. |
| 2019/0275331 A1 | 9/2019 | Zhu |
| 2019/0290900 A1 | 9/2019 | Esteller et al. |
| 2019/0299006 A1 | 10/2019 | Marnfeldt |
| 2019/0366094 A1 | 12/2019 | Esteller et al. |
| 2020/0155019 A1 | 5/2020 | Esteller et al. |

FOREIGN PATENT DOCUMENTS

| | | |
|---|---|---|
| WO | 2017/100866 | 6/2017 |
| WO | 2017/173493 | 10/2017 |
| WO | 2017/210352 | 12/2017 |
| WO | 2017/219096 | 12/2017 |

* cited by examiner

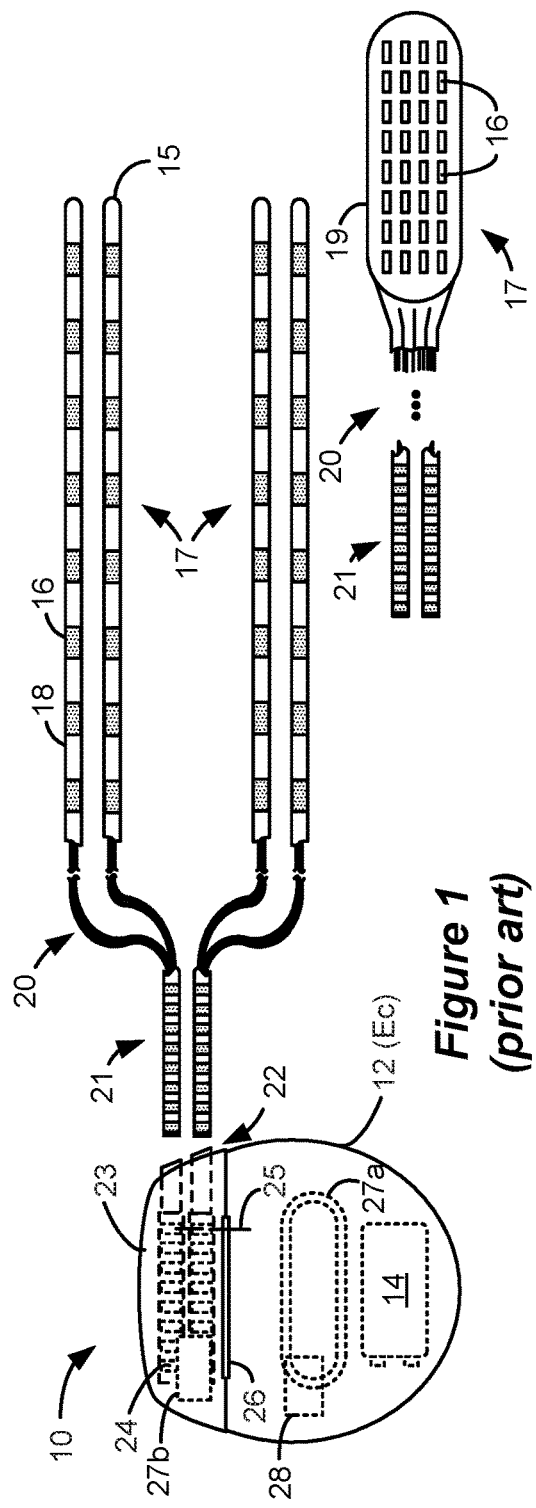
*Figure 1 (prior art)*
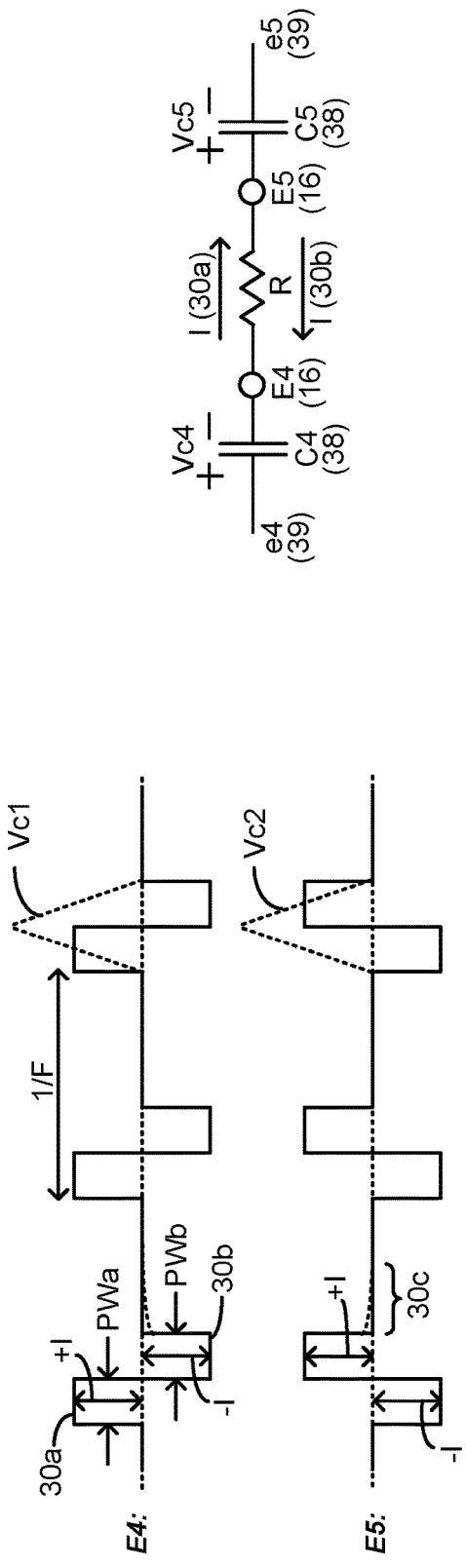
*Figure 2A (prior art)*
*Figure 2B (prior art)*

CIRCUITRY TO ASSIST WITH NEURAL SENSING IN AN IMPLANTABLE STIMULATOR DEVICE IN THE PRESENCE OF STIMULATION ARTIFACTS

CROSS REFERENCE TO RELATED APPLICATIONS

This is a continuation of U.S. patent application Ser. No. 16/821,602, filed Mar. 17, 2020, which is a non-provisional of U.S. Provisional Patent Application Ser. No. 62/825,981, filed Mar. 29, 2019. These applications are incorporated herein by reference in their entireties, and priority is claimed to them.

FIELD OF THE INVENTION

This application relates to Implantable Medical Devices (IMDs), and more specifically to circuitry to assist with sensing neural signals in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude +I to the tissue. Electrode E5 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown (FIG. 2A), and during the first phase 30a in which electrodes E4 and E5 are selected as an anode and cathode respectively, PDAC $40_4$ and NDAC $42_5$ are activated and digitally programmed to produce the desired current, I, with the correct timing (e.g., in accordance with the prescribed frequency F and pulse widths PWa). During the second phase 30b (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620,436, and U.S. Patent Application Publications 2018/0071520 and 2019/0083796. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27a and/or 27b), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30a followed thereafter by a second phase 30b of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30b of each pulse (Vc4=Vc5=0V), the first and second phases 30a and 30b are preferably charged balanced at each electrode, with the phases comprising an equal amount of charge but of the opposite polarity. In the example shown, such charge balancing is achieved by using the same pulse width (PWa=PWb) and the same amplitude (|+I|=|−I|) for each of the pulse phases 30a and 30b. However, the pulse phases 30a and 30b may also be charged balance if the product of the amplitude and pulse widths of the two phases 30a and 30b are equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced. Passive charge recovery typically occurs during at least a portion 30c (FIG. 2A) of the quiet periods between the pulses by closing passive recovery switches $41_i$. As shown in FIG. 3, the other end of the switches $41_i$ not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30a or 30b has a predominance of charge at a given electrode.

SUMMARY

An implantable medical device is disclosed, which may comprise: a first electrode node coupleable to a first electrode configured to make electrical contact with a patient's tissue, and a second electrode node coupleable to a second electrode configured to make electrical contact with the patient's tissue, wherein the first electrode node is configured to receive via the first electrode a tissue signal from the patient's tissue; an amplifier with a first input connected to the first electrode node and with a second input connected to the second electrode node, wherein the amplifier produces an amplifier output indicative of the tissue signal; first comparator circuitry configured to receive the first input and to generate a first output indicating whether the first input meets an input requirement of the amplifier; second comparator circuitry configured to receive the second input and to generate a second output indicating whether the second input meets an input requirement of the amplifier; and first logic circuitry configured to receive the first output and the second output and to generate an enable signal, wherein the enable signal indicates whether the amplifier output indicative of the tissue signal is valid or invalid.

In one example, the first and second electrode nodes comprise two of a plurality of electrodes nodes, and wherein the first and second electrodes comprise two of a plurality of electrodes, wherein each of the plurality of electrode nodes are coupleable to a different one the plurality of electrodes, wherein the plurality of electrodes are configured to make electrical contact with the patient's tissue. In one example, the implantable medical device further comprises a selector circuit configured to select the first and second electrode nodes from the plurality of electrode nodes. In one example, the implantable medical device further comprises stimulation circuitry configured to produce stimulation in the tissue via selected ones of the plurality of electrodes, wherein the tissue signal is generated in the patient's tissue in response to the stimulation. In one example, the second electrode comprises a conductive case of the implantable medical device. In one example, the implantable medical device further comprises a lead, wherein the lead comprises the first and second electrodes. In one example, a first blocking capacitor intervenes between the first electrode node and the first electrode, and wherein a second blocking capacitor intervenes between the second electrode node and the second electrode. In one example, the tissue signal comprises a neural response. In one example, the implantable medical device further comprises a first clamping circuit configured to keep a voltage at the first input from exceeding a first value, and a second clamping circuit configured to keep a voltage at the second input from exceeding the first value. In one example, the first clamping circuit is further configured to keep the voltage at the first input from going below a second value, and wherein the second clamping circuit is further configured to keep the voltage at the second input from going below the second value. In one example, the implantable medical device further comprises a first DC-level shifting circuit configured to set a DC voltage reference at the first input, and a second DC-level shifting circuit configured to set the DC voltage reference at the second input. In one example, the amplifier comprises a first input transistor with a first control terminal for receiving the first input, and a second input transistor with a second control terminal for receiving the second input, wherein the first and second input transistors comprise a threshold voltage that must respectively be exceeded at the first and second inputs to turn on the first and second transistors. In one example, the first comparator circuitry comprises a first comparator configured to indicate at the first output whether a voltage at the first input exceeds the threshold voltage, and wherein the second comparator circuitry comprises a second comparator configured to indicate at the second output whether a voltage at the second input exceeds the threshold voltage. In one example, the first comparator circuitry comprises: a first comparator configured to indicate whether a voltage at the first input exceeds a first voltage, a second comparator configured to indicate whether the voltage at the first input is below a second voltage, and second logic circuitry configured to receive the outputs of the first and second comparators and to generate the first output, wherein the first output indicates whether or not the voltage at the first input is between the first and second voltages; and wherein the second comparator circuitry comprises: a third comparator configured to indicate whether a voltage at the second input exceeds the first voltage, a fourth comparator configured to indicate whether the voltage at the second input is below the second voltage, and second logic circuitry configured to receive the outputs of the third and fourth comparators and to generate the second output, wherein the second output indicates whether or not the voltage at the second input is between the first and second voltages. In one example, the first voltage comprises a threshold voltage of input transistors in the amplifiers, and wherein the second voltage comprises a power supply voltage of the amplifier. In one example, the implantable medical device further comprises control circuitry configured to receive the amplifier output indicative of the tissue signal, wherein the control circuitry is programmed with an algorithm configured to analyze the amplifier output, wherein operation of the algorithm is controlled by the enable signal.

An implantable medical device is disclosed, which may comprise: a first electrode node coupleable to a first electrode configured to make electrical contact with a patient's tissue, wherein the first electrode node is configured to receive via the first electrode a tissue signal from the patient's tissue; an amplifier with a first input connected to the first electrode node and with a second input connectable to a reference voltage, wherein the amplifier produces an amplifier output indicative of the tissue signal; and comparator circuitry configured to receive the first input and to generate an enable signal indicating whether the first input meets an input requirement of the amplifier, wherein the enable signal indicates whether the amplifier output indicative of the tissue signal is valid or invalid.

In one example, the first electrode node comprises one of a plurality of electrodes nodes, and wherein the first electrode comprises one of a plurality of electrodes, wherein each of the plurality of electrode nodes are coupleable to a different one the plurality of electrodes, wherein the plurality of electrodes are configured to make electrical contact with the patient's tissue. In one example, the implantable medical device further comprises a selector circuit configured to select the first electrode nodes from the plurality of electrode nodes. In one example, the implantable medical device further comprises stimulation circuitry configured to produce stimulation in the tissue via selected ones of the plurality of electrodes, wherein the tissue signal is generated in the patient's tissue in response to the stimulation. In one example, the reference voltage comprises a DC voltage. In one example, the implantable medical device further comprises a lead, wherein the lead comprises the first electrode. In one example, a first blocking capacitor intervenes between the first electrode node and the first electrode. In one example, the tissue signal comprises a neural response. In one example, the implantable medical device further comprises a clamping circuit configured to keep a voltage at the first input from exceeding a first value. In one example, the clamping circuit is further configured to keep the voltage at the first input from going below a second value. In one example, the implantable medical device further comprises a DC-level shifting circuit configured to set a DC voltage reference at the first input. In one example, the amplifier comprises a first input transistor with a first control terminal for receiving the first input, and a second input transistor with a second control terminal for receiving the second input, wherein the first and second input transistors comprise a threshold voltage that must respectively be exceeded at the first and second inputs to turn on the first and second transistors. In one example, the comparator circuitry comprises a comparator configured to indicate at enable signal whether a voltage at the first input exceeds the threshold voltage. In one example, the comparator circuitry comprises: a first comparator configured to indicate whether a voltage at the first input exceeds a first voltage, a second comparator configured to indicate whether the voltage at the first input is below a second voltage, and logic circuitry configured to receive the outputs of the first and second comparators and to generate the enable signal, wherein the enable signal indicates whether or not the voltage at the first input is between the first and second voltages. In one example, the first voltage comprises a threshold voltage of input transistors in the amplifiers, and wherein the second voltage comprises a power supply voltage of the amplifier. In one example, the implantable medical device further comprises control circuitry configured to receive the amplifier output indicative of the tissue signal, wherein the control circuitry is programmed with an algorithm configured to analyze the amplifier output, wherein operation of the algorithm is controlled by the enable signal.

An implantable medical device is disclosed, which may comprise: a first electrode node coupleable to a first electrode configured to make electrical contact with a patient's tissue, and a second electrode node coupleable to a second electrode configured to make electrical contact with the patient's tissue, wherein the first electrode node is configured to receive via the first electrode a tissue signal from the patient's tissue; an amplifier with a first input connected to the first electrode node and with a second input connected to the second electrode node, wherein the amplifier produces a first amplifier output and a second amplifier output together comprising a differential amplifier output indicative of the tissue signal; comparator circuitry configured to determine from the first amplifier output a first comparator output indicating whether the first input meets an input requirement of the amplifier, and determine from the second amplifier output a second comparator output indicating whether the second input meets an input requirement of the amplifier; and logic circuitry configured to receive the first comparator output and the second comparator output and to generate an enable signal, wherein the enable signal indicates whether the differential amplifier output indicative of the tissue signal is valid or invalid.

In one example, the first and second electrode nodes comprise two of a plurality of electrodes nodes, and wherein the first and second electrodes comprise two of a plurality of electrodes, wherein each of the plurality of electrode nodes are coupleable to a different one the plurality of electrodes, wherein the plurality of electrodes are configured to make electrical contact with the patient's tissue. In one example, the implantable medical device further comprises a selector circuit configured to select the first and second electrode nodes from the plurality of electrode nodes. In one example, the implantable medical device further comprises stimulation circuitry configured to produce stimulation in the tissue via selected ones of the plurality of electrodes, wherein the tissue signal is generated in the patient's tissue in response to the stimulation. In one example, the second electrode comprises a conductive case of the implantable medical device. In one example, the implantable medical device further comprises a lead, wherein the lead comprises the first and second electrodes. In one example, a first blocking capacitor intervenes between the first electrode node and the first electrode, and wherein a second blocking capacitor intervenes between the second electrode node and the second electrode. In one example, the tissue signal comprises a neural response. In one example, the implantable medical device further comprises a first clamping circuit configured to keep a voltage at the first input from exceeding a first value, and a second clamping circuit configured to keep a voltage at the second input from exceeding the first value. In one example, the first clamping circuit is further configured to keep the voltage at the first input from going below a second value, and wherein the second clamping circuit is further configured to keep the voltage at the second input from going below the second value. In one example, the implantable medical device further comprises a first DC-level shifting circuit configured to set a DC voltage reference at the first input, and a second DC-level shifting circuit configured to set the DC voltage reference at the second input. In one example, the amplifier comprises a first input transistor with a first control terminal for receiving the first input, and a second input transistor with a second control terminal for receiving the second input, wherein the first and second input transistors comprise a threshold voltage that must respectively be exceeded at the first and second inputs to turn on the first and second transistors. In one example, the amplifier further comprises a first resistance serially connected between the first input transistor and a power supply voltage, and a second resistance serially connected between the second input transistor and the power supply voltage, wherein the first amplifier output comprises a node between the first input transistor and the first resistance, and wherein the second amplifier output comprises a node between the second input transistor and the second resistance. In one example, the comparator circuitry comprises: a first comparator configured to indicate whether a voltage at the first differential output is below a first voltage, a second comparator configured to indicate whether a voltage at the second differential output is below the first voltage. In one example, the amplifier is powered by a power supply voltage, and wherein the first voltage is less than the power supply voltage. In one example, the implantable medical device further comprises control circuitry configured to receive the differential amplifier output indicative of the tissue signal, wherein the control circuitry is programmed with an algorithm configured to analyze the amplifier output, wherein operation of the algorithm is controlled by the enable signal.

An implantable medical device is disclosed, which may comprise: a first electrode node coupleable to a first electrode configured to make electrical contact with a patient's tissue, wherein the first electrode node is configured to receive via the first electrode a tissue signal from the patient's tissue; an amplifier with a first input connected to the first electrode node and with a second input connectable to a reference voltage, wherein the amplifier produces a first amplifier output and a second amplifier output together comprising a differential amplifier output indicative of the tissue signal; and comparator circuitry configured to determine from the first amplifier output an enable signal indicating whether the first input meets an input requirement of the amplifier, wherein the enable signal indicates whether the differential amplifier output indicative of the tissue signal is valid or invalid.

In one example, the first electrode node comprises one of a plurality of electrodes nodes, and wherein the first electrode comprises one of a plurality of electrodes, wherein each of the plurality of electrode nodes are coupleable to a different one the plurality of electrodes, wherein the plurality of electrodes are configured to make electrical contact with the patient's tissue. In one example, the implantable medical device further comprises a selector circuit configured to select the first electrode nodes from the plurality of electrode nodes. In one example, the implantable medical device further comprises stimulation circuitry configured to produce stimulation in the tissue via selected ones of the plurality of electrodes, wherein the tissue signal is generated in the patient's tissue in response to the stimulation. In one example, the reference voltage comprises a DC voltage. In one example, the implantable medical device further comprises a lead, wherein the lead comprises the first electrode. In one example, a first blocking capacitor intervenes between the first electrode node and the first electrode. In one example, the tissue signal comprises a neural response. In one example, the implantable medical device further comprises a clamping circuit configured to keep a voltage at the first input from exceeding a first value. In one example, the clamping circuit is further configured to keep the voltage at the first input from going below a second value. In one example, the implantable medical device further comprises a DC-level shifting circuit configured to set a DC voltage reference at the first input. In one example, the amplifier comprises a first input transistor with a first control terminal for receiving the first input, and a second input transistor with a second control terminal for receiving the second input, wherein the first and second input transistors comprise a threshold voltage that must respectively be exceeded at the first and second inputs to turn on the first and second transistors. In one example, the amplifier further comprises a first resistance serially connected between the first input transistor and a power supply voltage, and a second resistance serially connected between the second input transistor and the power supply voltage, wherein the first amplifier output comprises a node between the first input transistor and the first resistance, and wherein the second amplifier output comprises a node between the second input transistor and the second resistance. In one example, the comparator circuitry comprises a comparator configured to indicate whether a voltage at the first differential output is below a first voltage. In one example, the amplifier is powered by a power supply voltage, and wherein the first voltage is less than the power supply voltage. In one example, the implantable medical device further comprises control circuitry configured to receive the differential amplifier output indicative of the tissue signal, wherein the control circuitry is programmed with an algorithm configured to analyze the amplifier output, wherein operation of the algorithm is controlled by the enable signal.

An implantable medical device is disclosed, which may comprise: a first electrode node coupleable to a first electrode configured to make electrical contact with a patient's tissue, and a second electrode node coupleable to a second electrode configured to make electrical contact with the patient's tissue, wherein the first electrode node is configured to receive via the first electrode a tissue signal from the patient's tissue; an amplifier with a first input connected to the first electrode node and with a second input connected to the second electrode node, wherein the amplifier produces an amplifier output indicative of the tissue signal; a first clamping circuit configured to keep a voltage at the first input from exceeding a first value; and a second clamping circuit configured to keep a voltage at the second input from exceeding the first value.

In one example, the first clamping circuit is further configured to keep the voltage at the first input from going below a second value, and wherein the second clamping circuit is further configured to keep the voltage at the second input from going below the second value. In one example, the first and second electrode nodes comprise two of a plurality of electrodes nodes, and wherein the first and second electrodes comprise two of a plurality of electrodes, wherein each of the plurality of electrode nodes are coupleable to a different one the plurality of electrodes, wherein the plurality of electrodes are configured to make electrical contact with the patient's tissue. In one example, the implantable medical device further comprises a selector circuit configured to select the first and second electrode nodes from the plurality of electrode nodes. In one example, the implantable medical device further comprises stimulation circuitry configured to produce stimulation in the tissue via selected ones of the plurality of electrodes, wherein the tissue signal is generated in the patient's tissue in response to the stimulation. In one example, the second electrode comprises a conductive case of the implantable medical device. In one example, the implantable medical device further comprises a lead, wherein the lead comprises the first and second electrodes. In one example, a first blocking capacitor intervenes between the first electrode node and the first electrode, and wherein a second blocking capacitor intervenes between the second electrode node and the second electrode. In one example, the tissue signal comprises a neural response.

An implantable medical device is disclosed, which may comprise: a first electrode node coupleable to a first electrode configured to make electrical contact with a patient's tissue, and a second electrode node coupleable to a second electrode configured to make electrical contact with the patient's tissue, wherein the first electrode node is configured to receive via the first electrode a tissue signal from the patient's tissue; an amplifier with a first input connected to the first electrode node and with a second input connected to the second electrode node, wherein the amplifier produces an amplifier output indicative of the tissue signal; a first DC-level shifting circuit configured to set a DC voltage reference at the first input; and a second DC-level shifting circuit configured to set the DC voltage reference at the second input.

In one example, the first and second electrode nodes comprise two of a plurality of electrodes nodes, and wherein the first and second electrodes comprise two of a plurality of electrodes, wherein each of the plurality of electrode nodes are coupleable to a different one the plurality of electrodes, wherein the plurality of electrodes are configured to make electrical contact with the patient's tissue. In one example, the implantable medical device further comprises a selector circuit configured to select the first and second electrode nodes from the plurality of electrode nodes. In one example, the implantable medical device further comprises stimulation circuitry configured to produce stimulation in the tissue via selected ones of the plurality of electrodes, wherein the tissue signal is generated in the patient's tissue in response to the stimulation. In one example, the second electrode comprises a conductive case of the implantable medical device. In one example, the implantable medical device further comprises a lead, wherein the lead comprises the first and second electrodes. In one example, a first blocking capacitor intervenes between the first electrode node and the first electrode, and wherein a second blocking capacitor intervenes between the second electrode node and the second electrode. In one example, the tissue signal comprises a neural response.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

DETAILED DESCRIPTION

Figure 4:
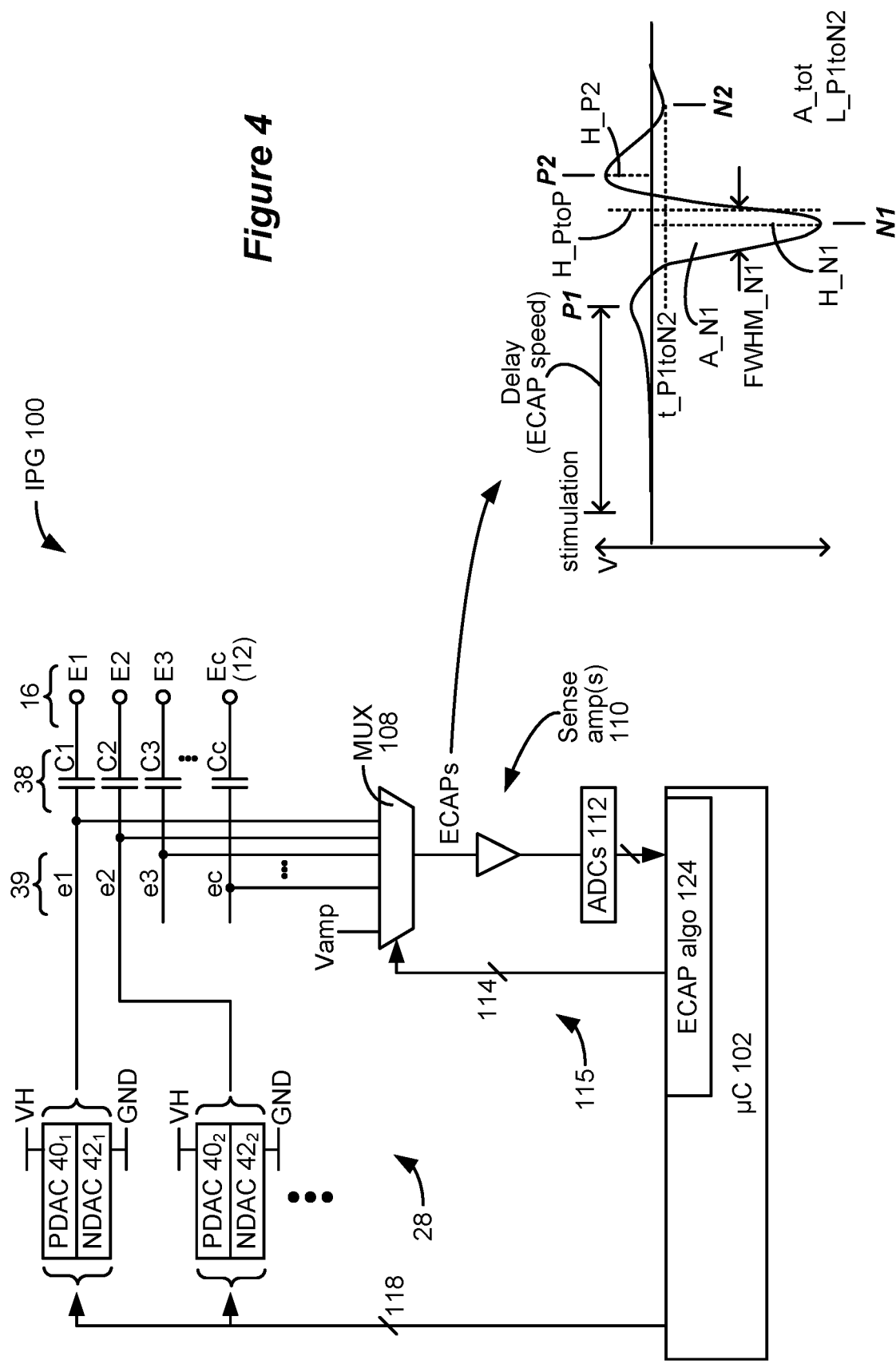
FIG. 4 shows an improved IPG having neural response sensing, and the ability to adjust stimulation dependent on such sensing.

An increasingly interesting development in pulse generator systems, and in Spinal Cord Stimulator (SCS) pulse generator systems specifically, is the addition of sensing capability to complement the stimulation that such systems provide. For example, and as explained in U.S. Patent Application Publication 2017/0296823, it can be beneficial to sense a neural response in neural tissue that has received stimulation from an SCS pulse generator. One such neural response is an Evoked Compound Action Potential (ECAP). An ECAP comprises a cumulative response provided by neural fibers that are recruited by the stimulation, and essentially comprises the sum of the action potentials of recruited fibers when they "fire." An ECAP is shown in FIG. 4, and comprises a number of peaks that are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 4, because an ECAP's shape is a function of the number and types of neural fibers that are recruited and that are involved in its conduction. An ECAP is generally a small signal, and may have a peak-to-peak amplitude on the order of tens of microVolts to tens of milliVolts.

Also shown in FIG. 4 is circuitry for an IPG 100 (or an ETS) that is capable of providing stimulation and sensing a resulting ECAP or other neural response or signal. The IPG 100 includes control circuitry 102, which may comprise a microcontroller for example such as Part Number MSP430, manufactured by Texas Instruments, which is described in data sheets at http://www.ti.com/lsds/ti/microcontroller/16-bit_msp430/overview.page? DCMP=MCU_other& HQS=msp430, which is incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an ECAP algorithm 124, described below) to one or more PDACs $40_i$ or NDACs $42_i$ to produce currents or voltages of prescribed amplitudes (I) for the stimulation pulses, and with the correct timing (PW, f). As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present, but are not shown in FIG. 4 for simplicity.

IPG 100 also includes sensing circuitry 115, and one or more of the electrodes 16 can be used to sense neural responses such as the ECAPs described earlier. In this regard, each electrode node 39 is further coupleable to a sense amp circuit 110. Under control by bus 114, a multiplexer 108 can select one or more electrodes to operate as sensing electrodes by coupling the electrode(s) to the sense amps circuit 110 at a given time, as explained further below. Although only one multiplexer 108 and sense amp circuit 110 is shown in FIG. 4, there could be more than one. For example, there can be four multiplexer 108/sense amp circuit 110 pairs each operable within one of four timing channels supported by the IPG 100 to provide stimulation. The analog waveform comprising the ECAP is preferably converted to digital signals by one or more Analog-to-Digital converters (ADC(s)) 112, which may sample the waveform at 50 kHz for example. The ADC(s) 112 may also reside within the control circuitry 102, particularly if the control circuitry 102 has A/D inputs. Multiplexer 108 can also provide a reference voltage, Vamp, to the sense amp circuit 110, as is useful in a single-ended sensing mode, as explained later with reference to FIGS. 10A and 10B.

So as not to bypass the safety provided by the DC-blocking capacitors 38, the input to the sense amp circuitry 110 is preferably taken from the electrode nodes 39, and so the DC-blocking capacitors 38 intervene between the electrodes 16 where the ECAPs are sensed and the electrode nodes 39. However, because the DC-blocking capacitors 38 will pass AC signals while blocking DC components, the AC ECAP signal will pass through the capacitors 38 and is still readily sensed by the sense amp circuit 110. In other examples, the ECAP may be sensed directly at the electrodes 16 without passage through intervening capacitors 38.

As shown, an ECAP algorithm 124 is programmed into the control circuitry 102 to receive and analyze the digitized ECAPs. One skilled in the art will understand that the ECAP algorithm 124 can comprise instructions that can be stored on non-transitory machine-readable media, such as magnetic, optical, or solid-state memories within the IPG 100 (e.g., stored in association with control circuitry 102).

In the example shown in FIG. 4, the ECAP algorithm 124 operates within the IPG 100 to determine one or more ECAP features, which may include but are not limited to:
- a height of any peak (e.g., H_N1) present in the ECAP;
- a peak-to-peak height between any two peaks (such as H_PtoP from N1 to P2);
- a ratio of peak heights (e.g., H_N1/H_P2);
- a peak width of any peak (e.g., the full width half maximum of a N1, FWHM_N1);
- an area under any peak (e.g., A_N1);
- a total area (A_tot) comprising the area under positive peaks with the area under negative peaks subtracted or added;
- a length of any portion of the curve of the ECAP (e.g., the length of the curve from P1 to N2, L_P1toN2)
- any time defining the duration of at least a portion of the ECAP (e.g., the time from P1 to N2, t_P1toN2);
- a time delay from stimulation to issuance of the ECAP, which is indicative of the neural conduction speed of the ECAP, which can be different in different types of neural tissues;
- any mathematical combination or function of these variables (e.g., H_N1/FWHM_N1 would generally specify a quality factor of peak N1).

Once the ECAP algorithm 124 determines one or more of these features, it may then adjust the stimulation that the IPG 100 provides, for example by providing new data to the stimulation circuitry 28 via bus 118. This is explained further in U.S. Patent Application Publications 2017/0296823 and 2019/0099602, which are incorporated herein by reference in their entireties. In one simple example, the ECAP algorithm 124 can review the height of the ECAP (e.g., its peak-to-peak voltage), and in closed loop fashion adjust the amplitude I of the stimulation current to try and maintain the ECAP to a desired value.

Figure 5A:
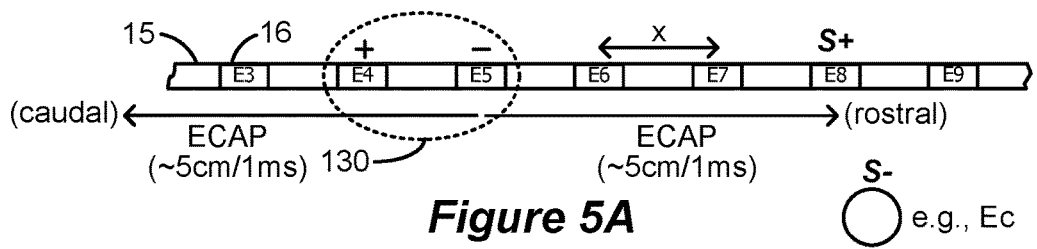
FIGS. 5A-5D shows stimulation producing a neural response, and the sensing of that neural response at least one electrode of the IPG using a differential amplifier.
Figure 5B:
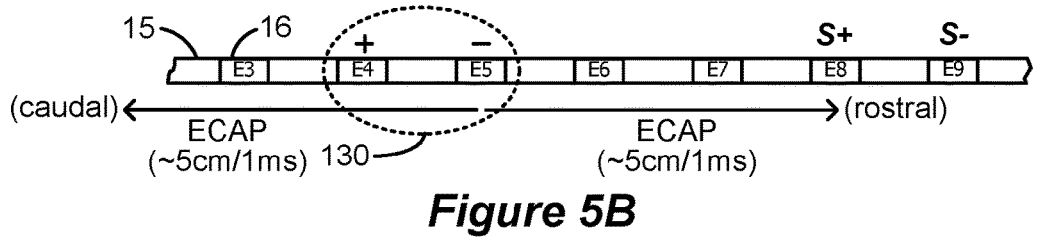

FIGS. 5A and 5B show a percutaneous lead 15, and show the stimulation program example of FIG. 2A in which electrodes E4 and E5 are used to produce pulses in a bipolar mode of stimulation, with (during the first phase 30*a*) E4 comprising an anode and E5 a cathode, although other electrode arrangements (e.g., tripoles, etc.) could be used as well. Such stimulation produces an electromagnetic (EM) field 130 in a volume of the patient's tissue around the selected electrodes. Some of the neural fibers within the EM field 130 will be recruited and fire, particularly those proximate to the cathodic electrode E5. Hopefully the sum of the neural fibers firing will mask signals indicative of pain in an SCS application, thus providing the desired therapy. The recruited neural fibers in sum produce an ECAP, which can travel both rostrally toward the brain and caudally away from the brain. The ECAP passes through the spinal cord by neural conduction with a speed which is dependent on the neural fibers involved in the conduction. In one example, the ECAP may move at a speed of about 5 cm/1 ms.

The ECAP is preferably sensed differentially using two electrodes, and FIGS. 5A and 5B show different examples. In FIG. 5A, a single electrode E8 on the lead 15 is used for sensing (S+), with another signal being used as a reference (S−). In this example, the sensing reference S− comprises a more distant electrode in the electrode array 17 or (as shown) the case electrode Ec. (However, reference S− could also comprise a fixed voltage provided by the IPG 100, such as ground, in which case sensing would be said to be single-ended instead of differential). In FIG. 5B, two lead-based electrodes are used for sensing, with such electrodes either being adjacent or at least relatively close to one another. Specifically, in this example, electrode E8 is again used for sensing (S+), with adjacent electrode E9 providing the reference (S−). This could also be flipped, with E8 providing the reference (S−) for sensing at electrode E9 (S+). Sensing a given ECAP at different electrodes can allow the ECAP algorithm 124 to understand the time difference between the arrival of the ECAP at each of the electrodes. If the distance x between the electrodes is known, the ECAP algorithm 124 can then compute speed of the ECAP. As noted above, ECAP speed is indicative of the neural fibers involved in neural recruitment and conduction, which can be interesting to know in its own right, and which may be useful to the ECAP algorithm 124 in adjusting the stimulation provided by the stimulation circuitry 28.

Figure 5C:
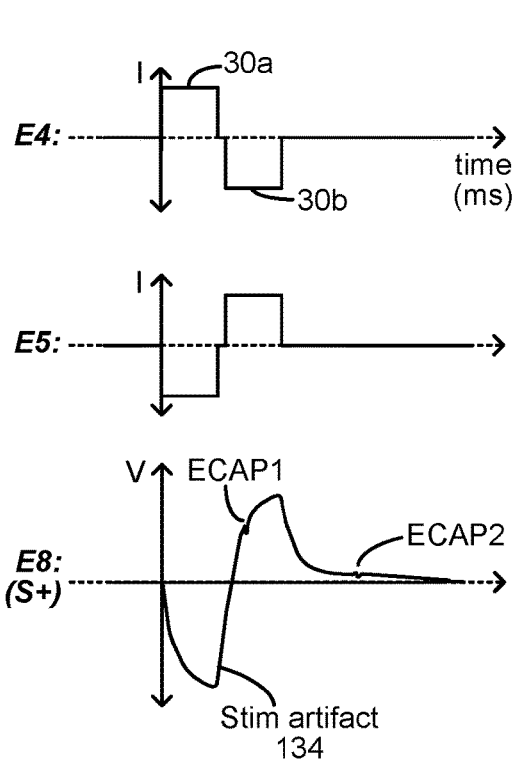

FIG. 5C shows waveforms for the stimulation program, as well as the signal that would appear in the tissue at sensing electrode E8 (S+). As well as including the ECAP to be sensed, the signal at the sensing electrode S+ also includes a stimulation artifact 134. The stimulation artifact 134 comprises a voltage that is formed in the tissue as a result of the stimulation, i.e., as result of the EM field 130. As described in U.S. Patent Application Publication 2019/0299006, which is incorporated herein by reference in its entirety, the PDACs and NDACs used to form the currents in the tissue have high output impedances. This can cause the voltage in the tissue to vary between ground and the compliance voltage VH used to power the DACs, which as noted earlier can be a high voltage (e.g., as high as 18V). The magnitude of the stimulation artifact 134 at a given sensing electrode S+ or its reference S− can therefore be high (e.g., several Volts), and significantly higher than the magnitude of the ECAP. The magnitude of the stimulation artifact 134 at the sensing electrodes S+ and S− is dependent on many factors. For example, the stimulation artifact 134 will be larger if the sensing electrodes are closer to the electrodes used to provide the stimulation (E4, E5). The stimulation artifact 134 is also generally larger during the provision of the pulses, although it may still be present even after the pulse (i.e., the last phase 30*b* of the pulse) has ceased due to the capacitive nature of the tissue, which keeps the electric field 130 from dissipating immediately.

The relatively large-signal background stimulation artifact 134 can make resolution and sensing of the small-signal ECAP difficult at the sense amp circuit 110. To ameliorate this concern, it can be beneficial to use a sensing electrode S+ that is far away from the stimulating electrodes. See, e.g., U.S. Patent Application Publication 2020/0155019, which is incorporated herein by reference in its entirety. This can be beneficial because the stimulation artifact 134 would be smaller at a distant sensing electrode, and because the ECAP would pass a distant sensing electrode at a later time when the stimulation artifact 134 might have dissipated (e.g., ECAP2 in FIG. 5C). However, using a distant sensing electrode is not always possible or practical. For one, the electrode array 17 may simply not be large enough, and therefore no electrode may be suitably far enough away from the stimulating electrodes to ideally operate as the sensing electrode. Likewise, the magnitude of the ECAP also diminishes as distance from the stimulating electrodes increases, and therefore while the stimulation artifact 134 would be smaller at a more distant sensing electrode, so too would the ECAP, again making sensing difficult.

Figure 3:
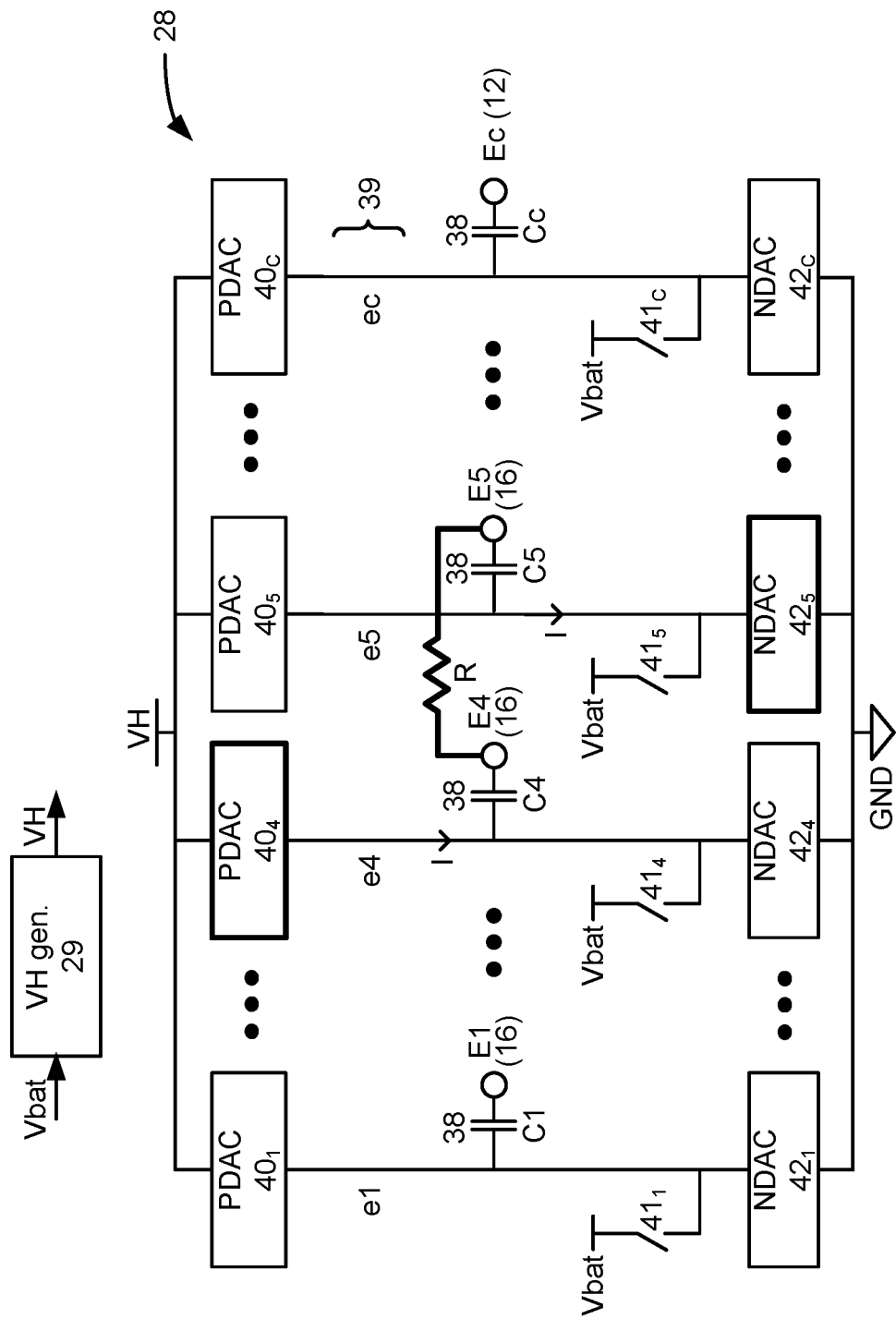
FIG. 3 shows stimulation circuitry useable in the IPG, in accordance with the prior art.

Sensing the ECAP may also be easier during periods when the stimulation artifact 134 is smaller. For example, and as shown in FIG. 5C, the stimulation artifact 134 can be relatively large during the time that the pulse (i.e., its phases) is issuing (30a and 30b), making sensing of ECAP (e.g., ECAP1) particularly difficult during that time. It may then be desirable to sense the ECAP after the pulse has ceased, when the stimulation artifact is smaller and decreasing (e.g., ECAP2). However, sensing the ECAP after cessation of the pulse is not always possible, depending on various factors. For example, if the sensing electrode S+ is close to the stimulating electrodes, if the pulse width of the pulse (or its phases) is relatively long, or if the speed of the ECAP is relatively fast, it cannot always be possible to sense the ECAP after cessation of the pulse. Also, it may be necessary to use passive charge recovery after the cessation of the pulse. As noted earlier, passive charge recovery involves shorting the electrode nodes 39 to a reference voltage (e.g., Vbat) through passive charger recovery switches $41_i$ (FIG. 3). ECAP sensing may be difficult when the passive charge recovery switches are closed, as the electrode node 39 carrying the ECAP to the sense amp circuit 110 would be shorted to the reference voltage during this time. It may therefore be necessary in certain circumstances to sense the ECAP during the provision of the pulse or one of its phases.

Figure 5D:
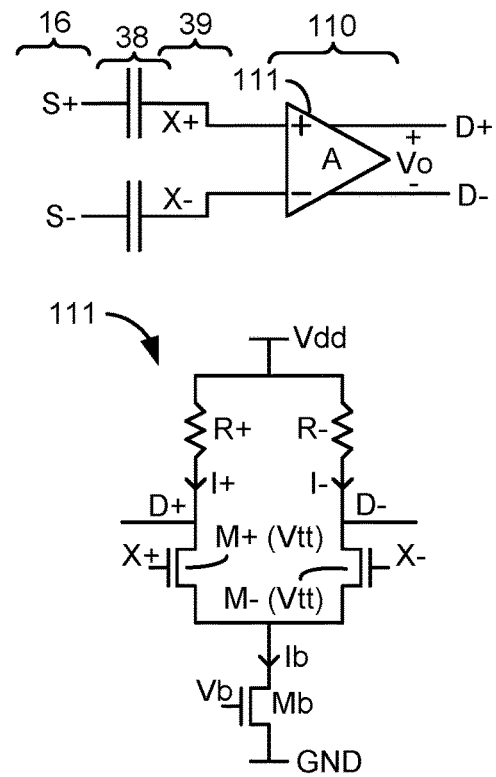

Differential sensing, in which the reference electrode S− is also exposed to the tissue and therefore to the stimulation artifact 134 to at least some degree, can assist ECAP resolution, and is shown in FIG. 5D. A simple example of sense amp circuit 110 is shown, which includes a differential amplifier 111. Also shown is a simple example of the circuitry within the differential amplifier 111, although it should be noted that many different differential amplifier circuits exist and can be used as well. Understand that the multiplexer 108 (FIG. 4) or other selector circuit could be present between the electrode nodes 39 and the differential amplifier 111, but this not shown in FIG. 5D for simplicity.

Sensing electrode S+ and sensing reference electrode S− are coupled through the DC-blocking capacitors 38 (if used) to derive signals X+ and X− at the electrode nodes 39 that are presented to the positive and negative inputs of the differential amplifier 111. As noted earlier, signals X+ and X− will be largely the same as S+ and S− present at the selected sensing electrodes, but with DC signal components removed. X+ and X− are provided to the gates (control terminals) of transistors M+ and M− in the differential amplifier 111. The drains of the transistors M+ and M− are connected to outputs D+ and D−, which in turn are coupled to the amplifier's power supply voltage Vdd via resistances R+ and R−. The sources of the transistors M+ and M− are connected to ground as the other power supply voltage through a common bias transistor Mb, which sets the total current Ib that, in sum, can pass through each of the legs (I+, I−) of the differential amplifier. Resistances R+ and R− are equal and are represented as simple resistors, although active devices (e.g., PMOS transistor) could also be used. The output of the amplifier 111, Vo, equals the difference in the voltages at outputs D+ and D−, which in turn is influenced by the difference in the signals present at X+ and X−. Signals X+ and X−, if different, will turn transistors M+ and M− on to different degrees, thus causing different currents I+ and I− to flow through each leg. This produces different voltage drops across the resistances R+ and R−, and thus different voltages at D+ and D−. In short, Vo=D+−D−=A(X+−X−), where A is the gain of the amplifier.

If the stimulation artifact 134 is present at both the sensing electrode S+ and reference electrode S−, the differential amplifier 111 will subtract the stimulation artifact as a common mode voltage from the output, ideally leaving only the ECAP to be sensed at the output. Note that the magnitude of the stimulation artifact 134 may not be exactly the same at sensing electrodes S+ and S−, which is not surprising as each is necessarily located at a different distance from the stimulating electrodes, and so common mode removal of the stimulation artifact may be not be perfect. Nevertheless, differential sensing allows the stimulation artifact 134 to be removed to at least some degree, making it easier to resolve the small-signal ECAP.

Differential sensing as illustrated in FIG. 5D can however be problematic, in particular because of limitations inherent in the differential amplifier 111. As noted earlier, the stimulation artifact 134 can vary by several Volts in the tissue, and X+ and X− may exceed the input requirements of the differential amplifier 111. Note that the differential amplifier 111 is powered by a power supply Vdd. This power supply Vdd is typically on the order of 3.3V or so, thus allowing the differential amplifier 111 to be simply and conveniently made from standard low voltage transistors such as M+ and M−. While the differential amplifier 111 can still work if X+ and X− are slightly higher than Vdd, amplifier operation would eventually be compromised if X+ and X− are significantly higher, which is entirely possible depending on the circumstances. Further, if X+ and X− are too high, the input transistors M+ and M− can become damaged, rendering the differential amplifier 111 non-functional.

X+ and X− can also be too low to allow for accurate sensing. In this regard, the input transistors M+ and M− are in this example NMOS transistors which have inherent gate threshold voltages (e.g., Vtt=0.7V), meaning that X+ and X− at the gate of these transistors must be above Vtt to turn the transistors on and to produce appreciable currents I+ and I− in each leg. If X+ or X− are lower than Vtt, I+ and I− will not flow to a significant degree. This means that the ECAP present in X+ may not be detected, or that the common mode voltage provided by the stimulation artifact 134 will not be properly subtracted by the differential amplifier 111.

In short, inputs X+ and X− in the sense amp circuitry 110 should be higher than the threshold voltages of the input transistors M+ and M−, and (preferably) below the differential amplifier 111's power supply voltage Vdd. Further, because X+ and X− can be high enough to damage the differential amplifier 111, further considerations in the sense amp circuit 110 are desired to ensure that this does not happen.

Figure 6A:
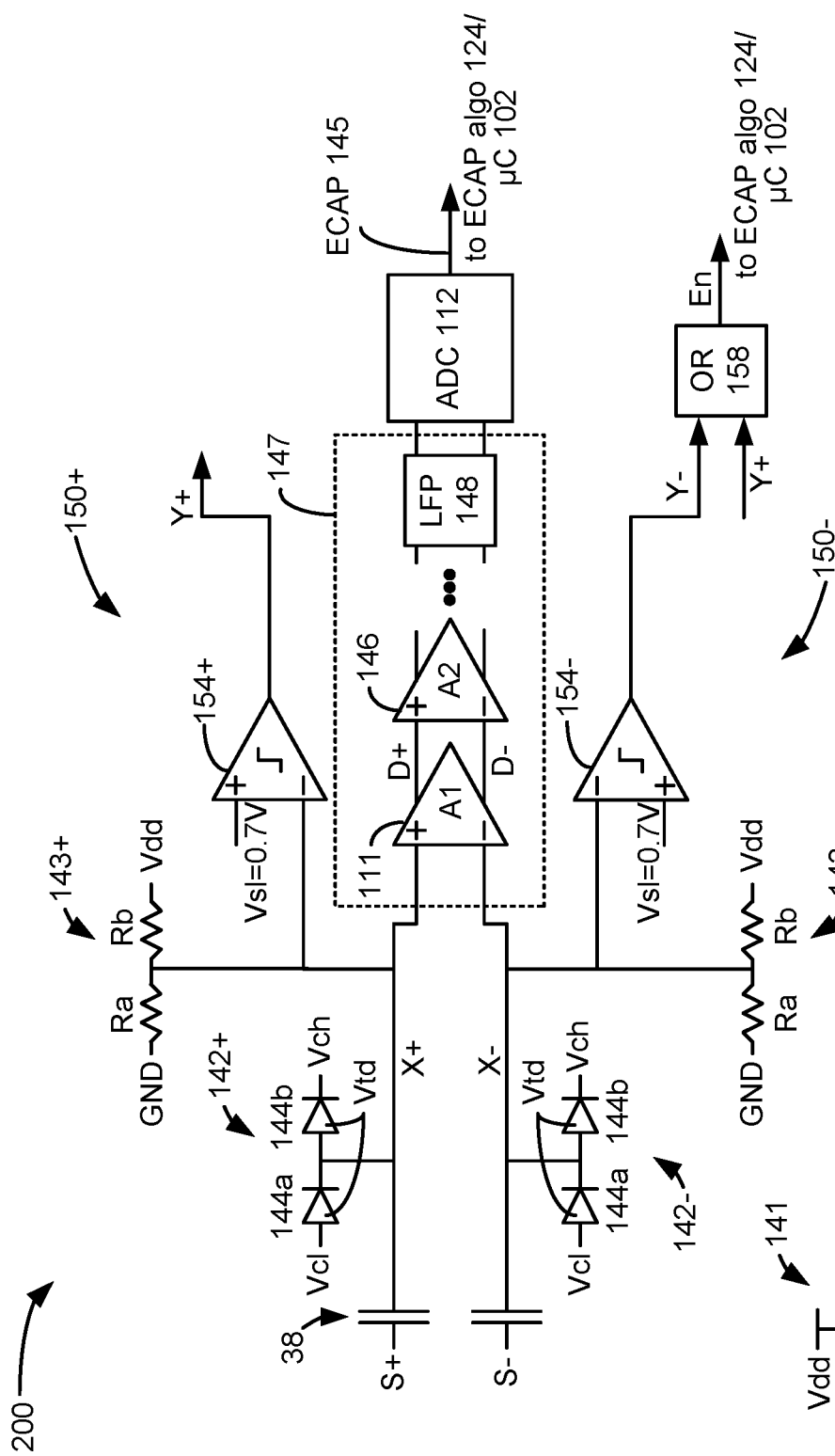
FIGS. 6A and 6B show a first example of a sense amp circuit with a differential amplifier for sensing a neural response, including a clamp circuit for the inputs of the differential amplifier, comparator circuitries for determining if the magnitude of the inputs are too low, and logic circuitry for generating an enable signal informing when the output of the differential amplifier is valid.
Figure 6B:
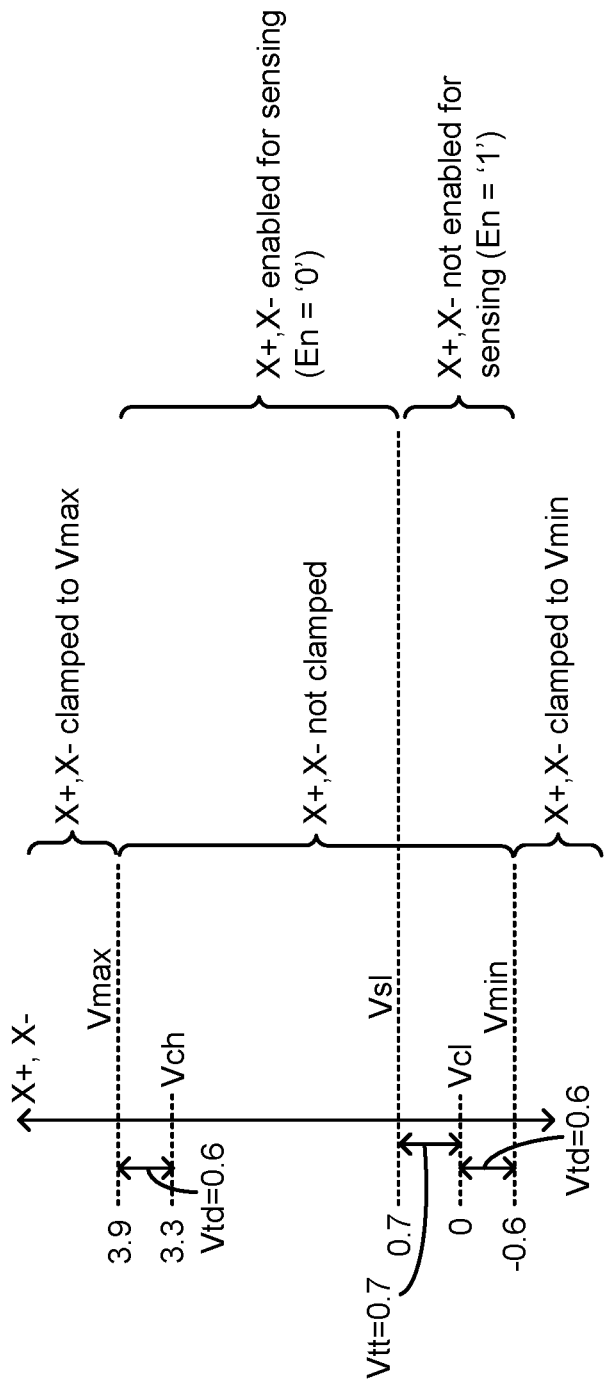

FIGS. 6A and 6B describe a first example of a sense amp circuit 200 designed to address these concerns, and includes additional circuitry to supplement the differential amplifier 111. As well as providing the ECAP signal to the control circuitry 102/ECAP algorithm 124 for analysis at output 145, the sense amp circuit 200 provides one or more enable signals (e.g., En) to inform the ECAP algorithm 124 when X+ and X− are of a magnitude such that the ECAP algorithm 124 can consider the ECAP at output 145 to be valid. As explained further below, enable signal En is issued as valid when X+ and X− are of a magnitude that is consistent with the input requirements of the differential amplifier 111.

As a preliminary matter, note that differential amplifier 111 may provide its output to various processing circuits 147 prior to presentation to the control circuitry 102 and the ECAP algorithm 124. For example, the differential amplifier 111's differential output (D+ and D−) may be provided to the inputs of another differential amplifier 146, and to still further differential amplifiers in series, etc. This can be helpful in increasing the gain of the detected ECAP signal, because the gains of each amplifier stage will multiply (A1*A2, etc.). A follower circuit or buffer could also be used in series as part of the processing circuitry 147 between the differential amplifier 111 and the ADC 112 but such stages are not shown. Further, the processing circuitry 147 may include a Low Pass Filter (LPF) 148 to remove high-frequency components in the ECAP signal that are not of interest, or that are inconsistent with the rate at which the ADC 112 will sample the signal. In one example, the LFP 148 removes frequency components of 25 kHz or higher. Processing circuitry 147 may be considered part of the control circuitry 102.

To prevent damage to or improper operation of the differential amplifier 111 (i.e., the first differential amplifier in series), inputs X+ and X− are provided with clamping circuits 142+ and 142− respectively. In the example shown, clamping circuit 142+ comprises a serial connection of diodes 144a and 144b which are forward biased between a low clamp reference voltage reference (Vcl) and a high clamp reference voltage (Vch), and with signal X+ connected to a node between the diodes. Vcl and Vch preferably comprise ground and the power supply voltage Vdd (e.g., 3.3V). In this example, it is assumed that the diodes 144a and 114b have a forward biased threshold voltage (Vtd) of 0.6V. Diode 144a would conduct (turn on) if the voltage at X+ is less than −0.6 Volts. Because such conductance is of very low resistance, X+ is effectively clamped to a minimum of Vmin=−0.6 Volts. If it is assumed that Vdd=3.3 V, diode 144b would conduct if X+ is greater than 3.9V Volts, which would clamp X+ to a maximum of Vmax=3.9V. If the voltage at X+ is at or between −0.6 and 3.9 Volts, neither diode 144a nor 144b in clamping circuit 142+ would conduct. Clamping circuit 142− is similar, but connects to signal X−, and so similarly clamps X− to a voltage at or between −0.6 and 3.9 Volts.

To summarize, clamping circuits 142+ and 142− allow X+ and X− to pass to the inputs of the differential amplifier 111 without clamping if they are between −0.6 and 3.9 Volts, but otherwise clamps voltages on these signals from exceeding 3.9 Volts or from being lower than −0.6V. This protects the differential amplifier 111. As noted above, if the inputs X+ or X− are significantly higher than the power supply voltage Vdd, the input transistors M+ and M− may become damaged. Further, if inputs X+ or X− are too low, the amplifier 111 may also not function properly, because the sources of drains of those transistors M+ and M− may start to leak to the substrate of those transistors.

Modifications may be made to the clamping circuits 142+ and 142− to adjust the window of permissible voltages at which clamping does not occur. For example, Vcl and Vch could be generated by their own generator circuits (similar to 141, discussed below) to produce unique values different from ground and Vdd. More than two diodes may also be used in series; for example, four diodes could be used in series, and if X+ or X− is connected between the middle two, this would expand the window to voltages from −1.2V (ground −2 Vtd) to 4.5V (Vdd+2 Vtd). Zener diodes could also be used, which could break down and thus clamp X+ or X− at specified reverse bias voltages.

The sense amp circuit 200 further includes DC-level shifting circuits 143+ and 143− to set signals X+ and X− to a DC voltage reference consistent with the input requirements for the differential amplifier 111. As discussed above, the differential amplifier 111 can only operate reliably if signals X+ and X− are of a magnitude that causes current I+ and I− to flow in each leg of the amplifier. In this regard, to sense the small-signal ECAP, X+ and X− should be higher than the threshold voltage of the amplifier's input transistors M+ and M− (e.g., greater than Vtt=0.7 V). It is further preferred that X+ and X− not exceed the power supply voltage Vdd of the differential amplifier (e.g., Vdd=3.3V) for proper amplifier operation. Accordingly, signals provided to the differential amplifier 111 are preferably referenced with respect to a DC voltage reference within this operating range. This reference could comprise ½ Vdd (e.g., 1.65 V), which comprises a midpoint between Vdd and ground. More preferably, the DC voltage reference could comprise ½(Vdd−Vtt)+Vtt (e.g., 2.0 V), as this value would be midpoint within the operating range 0.7V and 3.3V, and thus allow X+ and X− to symmetrically swing +/−1.3V from the reference while still providing an input magnitude suitable to operate the differential amplifier 111.

The magnitude of the DC voltage reference can be set at signals X+ and X− via DC-level shifting circuits 143+ and 143−. While such circuits can take different forms, in the example shown they comprise a resistor ladder, comprising resistors Ra and Rb in series biased between Vdd and ground, with signals X+ and X− connected to nodes between the resistors. This sets the DC voltage reference of both X+ and X− to Ra/(Ra+Rb)*(Vdd−ground). Thus by setting the values of Ra and Rb appropriately, the DC voltage reference can be set to any desired value between Vdd and ground, such as 2.0 V. AC signals then coupling to X+ and X− through the capacitors 38 (such as the ECAP and/or the stimulation artifact 134) will then be referenced to (and ride on top of) this DC voltage reference. As a general matter, this allows the differential amplifier 111 to be affected by the ECAP at X+, because the superposition of the ECAP and the DC voltage reference will cause a change in current I+. Preferably, Ra and Rb are large resistances, such 1 Mega-Ohm or higher.

Also present in sense amp circuitry 200 are comparator circuitries 150+ and 150−, which are connected to signals X+ and X− respectively. The goal of comparator circuitries 150+ and 150− are to respectively determine whether signals X+ and X− are of a reliable magnitude to sense ECAPs, and to indicate the same to the ECAP algorithm 124 via generation of an enable signal, En. Even though a DC voltage reference (e.g., 2.0 V) is established at X+ and X− by DC-level shifting circuits 143+ and 143−, the AC nature of the stimulation artifact 134 can cause large variations from this baseline. The enable signal En may change from time to time depending on the voltages at X+ and X−, and thus there may be times when the enable signal indicates to the ECAP algorithm 124 that output 145 is providing reliable ECAP data that is valid to assess at output 145 ('0'), and times when it indicates that output 145 is not producing reliable ECAP data and can be ignored ('1').

Comparator circuitry 150+ includes a comparator 154+ which receives X+ at its negative input, and a low sense reference voltage Vsl at its positive input. In one example, Vsl is set by a voltage generator 141 to a value that ensures that X+ is high enough to properly turn on transistor M+ in the differential amplifier 111. Many different types of generator circuits can be used to produce Vsl, including bandgap generator circuits, but FIG. 6A shows use of a simple resistor in series with an adjustable current source to set Vsl to the correct value. In one example, Vsl equals (or could be slightly higher than) the threshold voltage of M+, i.e., Vsl=Vtt−0.7V. If X+ is higher than Vsl, the comparator 154+ will output a '0' at signal Y+; by contrast, if X+ is lower than Vsl, the comparator will output a '1' at signal Y+. Comparator circuitry 150− is similar in construction and operation to comparator circuity 150+, and includes a comparator 154− to compare X− to Vsl and to determine when X− is suitably high (Y−='0') or too low (Y−='1').

While signals Y+ and Y− could be sent to control circuitry 102/ECAP algorithm 124 to operate as separate enable signals, in a preferred example, these signals are provided to logic circuitry such as an OR gate 158, which produces a single enable signal, En. Thus, if either Y+ or Y− equals '1', meaning that either X+ or X− is too low to properly operate the differential amplifier, En='1'. The ECAP algorithm 124 can therefore ignore ECAPs reported at output 145 in this circumstance, and instead only consider as valid ECAPs reported when En='0', where Y+ and Y− are both '0'. FIG. 6B summarizes operation of the sense amp circuit 200, showing windows for X+ and X− where they are not clamped (between Vmax=3.9 and Vmin=0.6), and showing a window where they are suitable for sensing (greater than Vsl=0.7). Note that the sensing window is effectively capped at Vmax, because V+ and V− cannot exceed this value.

Note that the magnitude of Vsl, and perhaps operation of the comparators 154+ and 154−, could depend on the manner in which the differential amplifier 111 is built. For example, if transistors M+ and M− in the differential amplifier 111 are PMOS transistors, Vsl could instead comprise a high sense reference voltage Vsh (e.g., Vdd−Vtt) that is provided to negative inputs of the comparators 154+ and 154−, with X+ and X− being provided to positive inputs of the comparators. If X+ or X− are below Vsh as would be necessary for proper differential amplifier 111 operation in this circumstance, the comparators 154+ or 154− would output a '0', and En='0', indicating to the ECAP algorithm 124 that ECAPs can be reliably sensed. If either of X+ or X− were above Vsh, En='1', indicating the opposite.

Figure 7A:
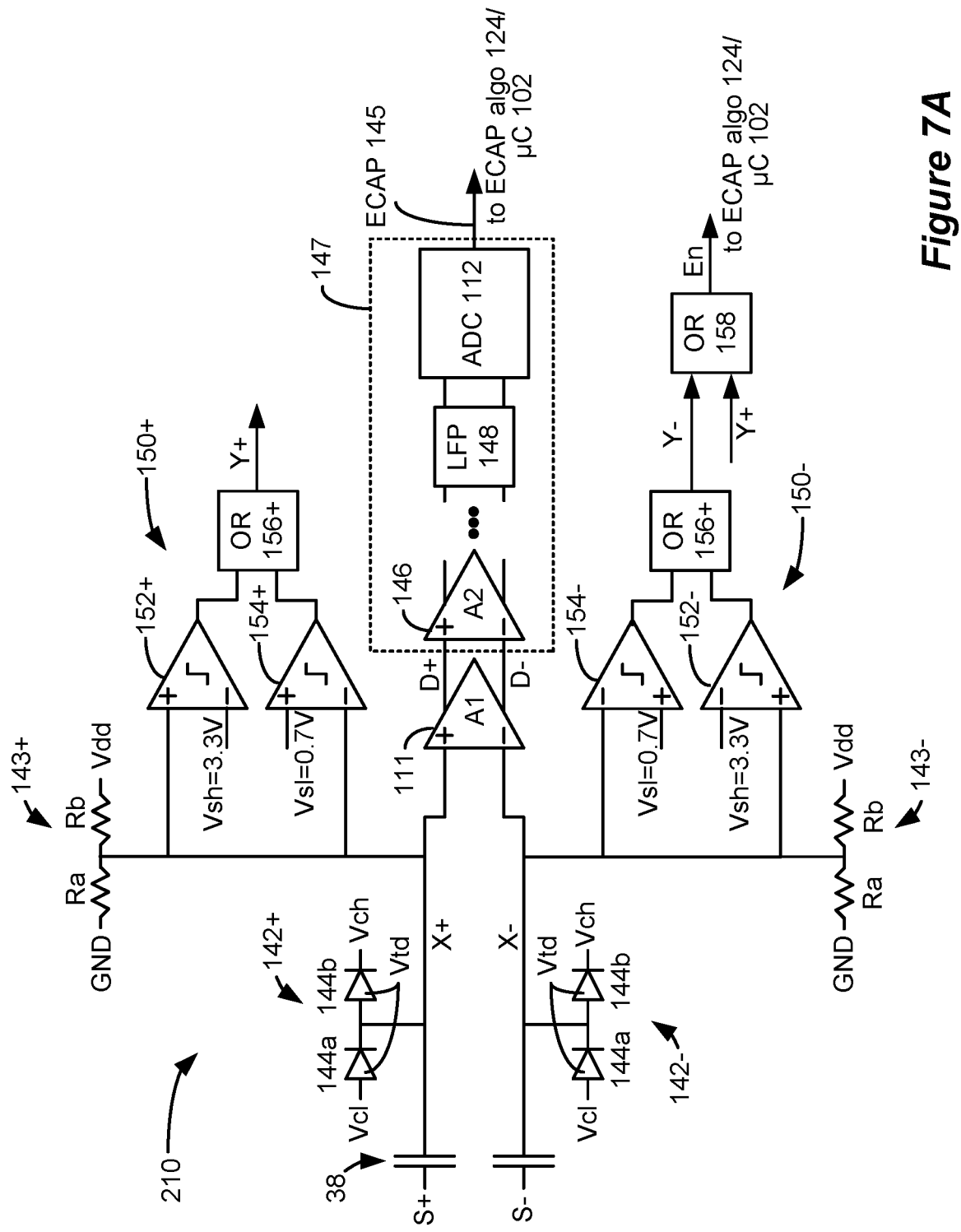
FIGS. 7A and 7B show a second example of a sense amp circuit similar to FIGS. 6A and 6B, but includes comparator circuitries for determining if the magnitude of the inputs are too low or too high.
Figure 7B:
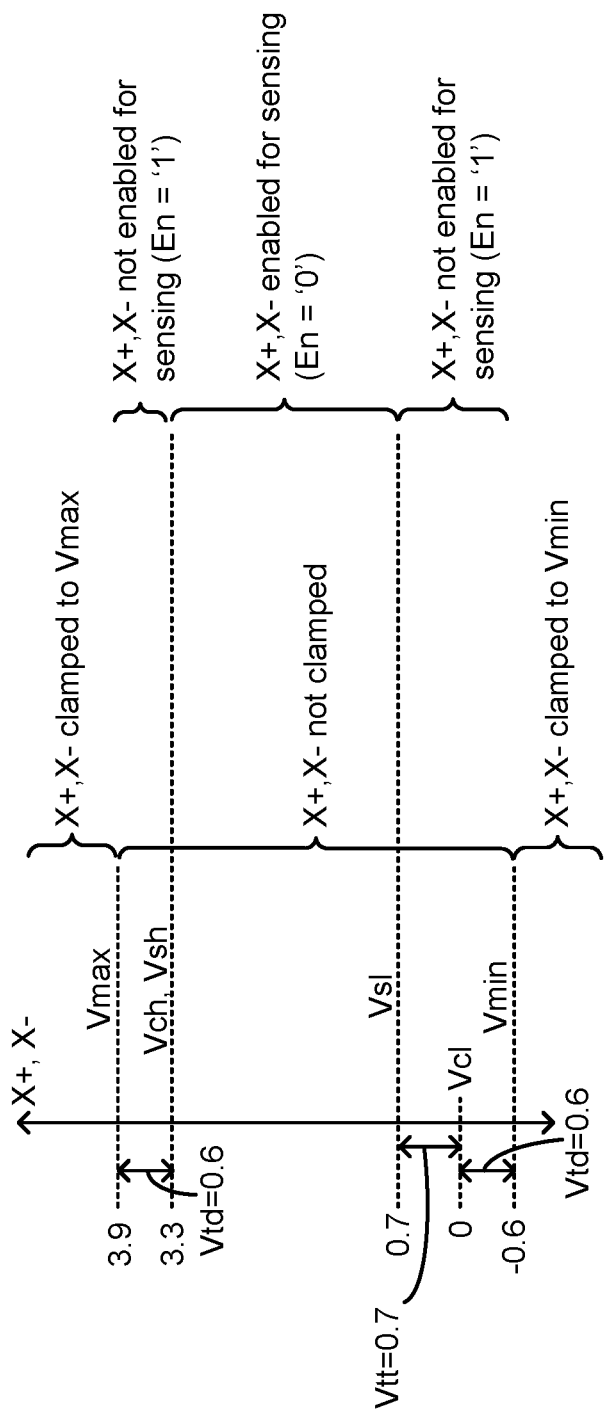

FIGS. 7A and 7B describe a second example of a sense amp circuit 210. Sense amp circuit 210 is similar to sense amp circuit 200, and includes clamp circuits 142+ and 142− and DC-level shifting circuits 143+ and 143− as described earlier. However, the comparators circuitries 150+ and 150− include additional comparators 152+ and 152− respectively. While comparators 154+ and 154− are designed to inform when X+ and X− are too low for valid ECAP sensing, comparators 152+ and 152− are designed to inform when X+ and X− are too high for valid ECAP sensing. In this regard, even though the clamp circuits 142+ and 142− would clamp X+ and X− to a maximum voltage Vmax (e.g., 3.9V), it may still be desirable to enable ECAP sensing only if X+ and X− are below this maximum. As noted earlier, high values for X+ and X− can also adversely affect differential amplifier 111 operation, even if such high values do not risk damaging the amplifier. Furthermore, ECAP sensing will not be reliable if X+ and X− are significantly high to cause diodes 144b in the clamp circuits 142+ and 142− to conduct.

In this regard, X+ and X− are sent to the positive inputs of comparators 152+ and 152−. The negative inputs are provided a high sense reference voltage Vsh. Like Vsl, Vsh can be set to different values (using a generator circuit like 141), but in a preferred example, Vsh is set to the power supply voltage Vdd (e.g., 3.3V). In this manner, comparators 152+ and 152− respectively output a '1' if X+ or X− are greater than Vsh. In comparator circuitry 150+, the outputs of comparators 152+ and 154+ are provided to logic circuitry such an OR gate 156+, which outputs signal Y+. Likewise, in comparator circuitry 150−, the outputs of comparators 152− and 154− are provided to an OR gate 156−, which outputs signal Y−. Signal Y+ informs whether X+ is too high ('1'), too low ('1'), or suitable for ECAP sensing ('0'), and signal Y− similarly informs whether X− is too high ('1'), too low ('1'), or suitable for ECAP sensing ('0'). As in circuit 200 (FIG. 6A), these outputs Y+ and Y− are provided to an OR gate 158 to produce the enable signal En for ECAP sensing. FIG. 7B summarizes operation of the sense amp circuit 210, showing windows for X+ and X− where they are not clamped (between Vmax=3.9 and Vmin=0.6), and showing a window where they are suitable for sensing (between Vsl=0.7 and Vsh=3.3V). The sense amp circuit 210 is preferred because the sensing window is smaller than and within the window where clamping does not occur. This way, ECAP sensing is disabled (En='1') before the X+ or X− becomes too large or too small to be clamped by their clamp circuits 142+ and 142−.

Comparator circuitries 150+ and 150− need not necessarily comprise discrete comparators such as 152+, 152−, 154+, and 154+. Instead, comparator circuitries 150+ and 150− may include Analog-to-Digital converters (ADCs) to produce digital representations of X+ and X−, which may comprise discrete circuits, or which may comprise ADC inputs of the control circuitry 102. The digitized values for X+ and X− may then be digitally compared (e.g., in the control circuitry 102) to various thresholds to determine whether they meet the input requirements of the differential amplifier 111, e.g., to see if X+ and X− are each between Vsl and Vsh. The result of these determinations can be expressed as a digital signals Y+ and Y− (e.g., again in the control circuitry 102), which are used by logic circuitry (e.g., again in the control circuitry 102) to determine the enable signal, En. In this regard, note that comparator circuities 150+ and 150− may be formed, at least in part, in the control circuitry 102 or using other digital logic circuits.

Figure 8:
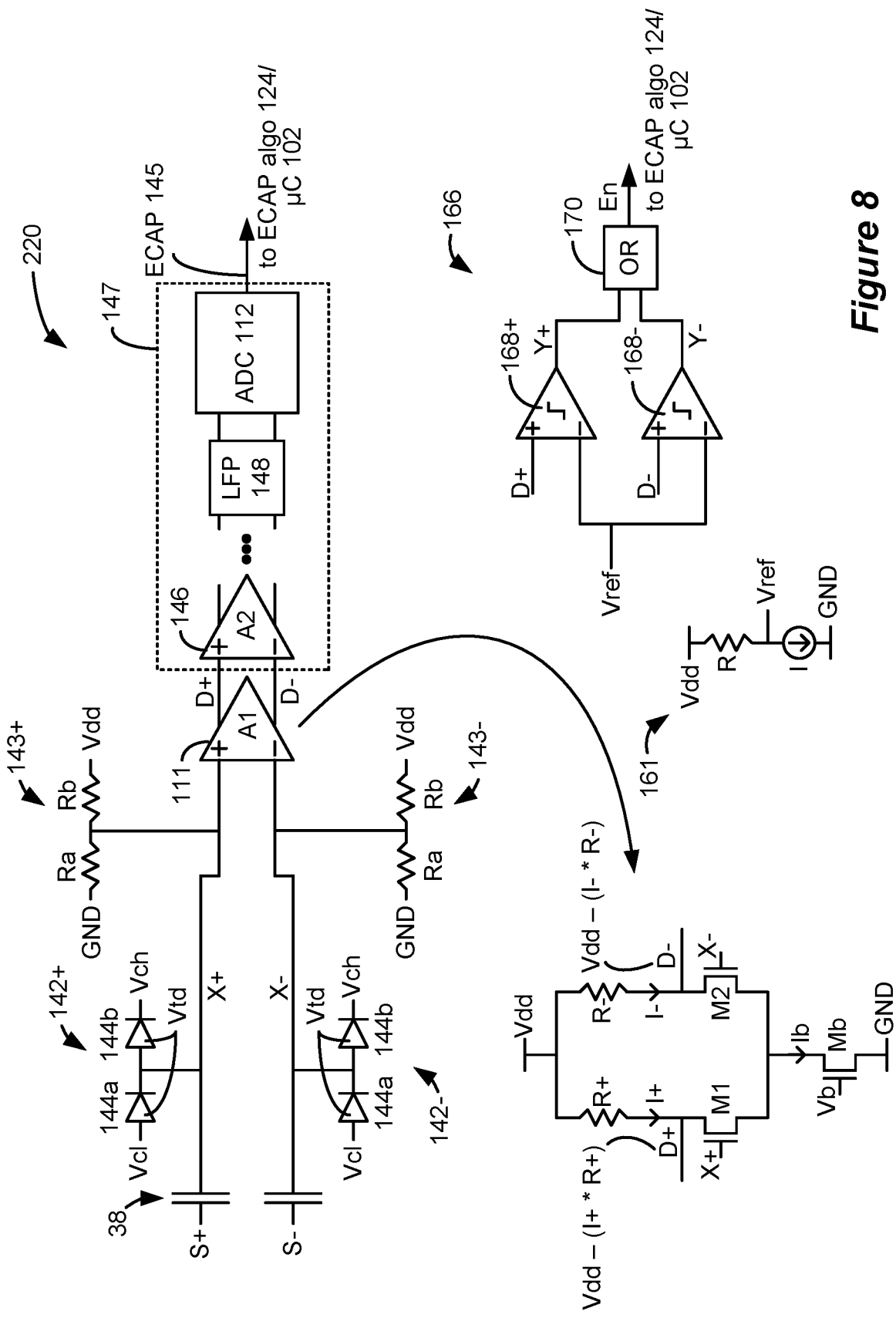
FIG. 8 shows a third example of a sense amp circuit similar to the above, including comparator circuities for determining if the outputs of the differential amplifier are valid for sensing, and generating an enable signal informing when the output of the differential amplifier is valid.

FIG. 8 shows another example of a sense amp circuit 220. As with other examples, sense amp circuit 220 includes clamp circuits 142+ and 142− to clamp X+ and X− to a maximum (Vmax) and preferably also minimum (Vmin) values. However, in sense amp circuit 220, whether ECAP sensing is indicated, and the value of enable signal En, is set by comparator circuitry 166 that differs compared to comparator circuitries 150+ and 150− described earlier. Instead, in sense amp circuit 220, comparator circuitry 166 effectively measures the current I+ and I− in each leg of the differential amplifier 111 to ensure that both legs are producing suitable currents indicative of proper amplifier operation.

As noted earlier, the differential amplifier 111 can only operate to sense ECAPs if both transistors M+ and M− are on to produce significant currents I+ and I− in their legs. In this regard, differential amplifier outputs D+ and D− may be assessed by comparator circuitry 166 to verify whether such currents are flowing. In the example of differential amplifier 111, leg currents I+ and I− flow through resistors R+ and R−, such that D+ equals Vdd−(I+*R+) and D− equals Vdd−(I−*R−). D+ and D− are therefore lower if significant currents I+ and I− are flowing. If these currents are too small or insignificant, D+ and D− will be too high.

Accordingly, comparator circuitry 166 can include comparators 168+ and 168− to gauge the magnitude of differential outputs D+ and D−, which as just noted are indicative of the currents I+ and I− flowing through the differential amplifier's legs and hence compliance with the amplifier's input requirements. Comparator 168+ receives D+ at its positive input, while comparator 168− receives D− at its positive input. The negative inputs of both comparators 168+ and 168− are set to a reference voltage, Vref, by a generator circuit 161. Again, generator circuit can take different forms, but is shown in FIG. 8 as an adjustable current in series with a resistance R. Vref is preferably just slightly below power supply voltage Vdd, such as 150 mV less than Vdd. These outputs Y+ and Y− can be sent to an OR gate 170 to produce the enable signal En that informs the ECAP algorithm 124 whether the ECAP signal present at output 145 is valid for ECAP sensing. If both of I+ or I− in the differential amplifier 111 are significant (because X+ and X− are significantly high), both of D+ or D− will be lower than Vref, and both of comparators 168+ or 168− will output a '0' for Y+ and Y−. OR gate 170 in turn outputs the enable signal En as a '0', indicating that the ECAP at output 145 is valid to sense. By contrast, if either or both of I+ or I− in the differential amplifier 111 are too small (because either or both of X+ or X− are too low), either or both of D+ or D− will be higher than Vref, and either or both of comparators 168+ or 168− will output a '1'. OR gate 170 in turn outputs the enable signal En as a '1', indicating to the ECAP algorithm 124 that the output 145 does not carry a valid and reliable ECAP signal, and hence that the output 145 should be ignored.

Comparator circuitry 166, like 150+ and 150−, need not necessarily comprise discrete comparators such as 168+ and 168−. Comparator circuitry 166 may include Analog-to-Digital converters (ADCs) to produce digital representations of D+ and D−, which may comprise discrete circuits, or which may comprise ADC inputs of the control circuitry 102. The digitized values for D+ and D− may then be digitally compared (e.g., in the control circuitry 102) to Vref. The result of these determinations can be expressed as a digital signals Y+ and Y− (e.g., again in the control circuitry 102), which are used by logic circuitry (e.g., again in the control circuitry 102) as above to determine the enable signal, En. Thus, as with comparator circuitries 150+ and 150−, comparator circuitry 166 may be formed, at least in part, in the control circuitry 102 or using other digital logic circuits.

As in other examples, the sense amp circuitry 220 may be modified depending on the type of differential amplifier 111 that is used.

Figure 9:
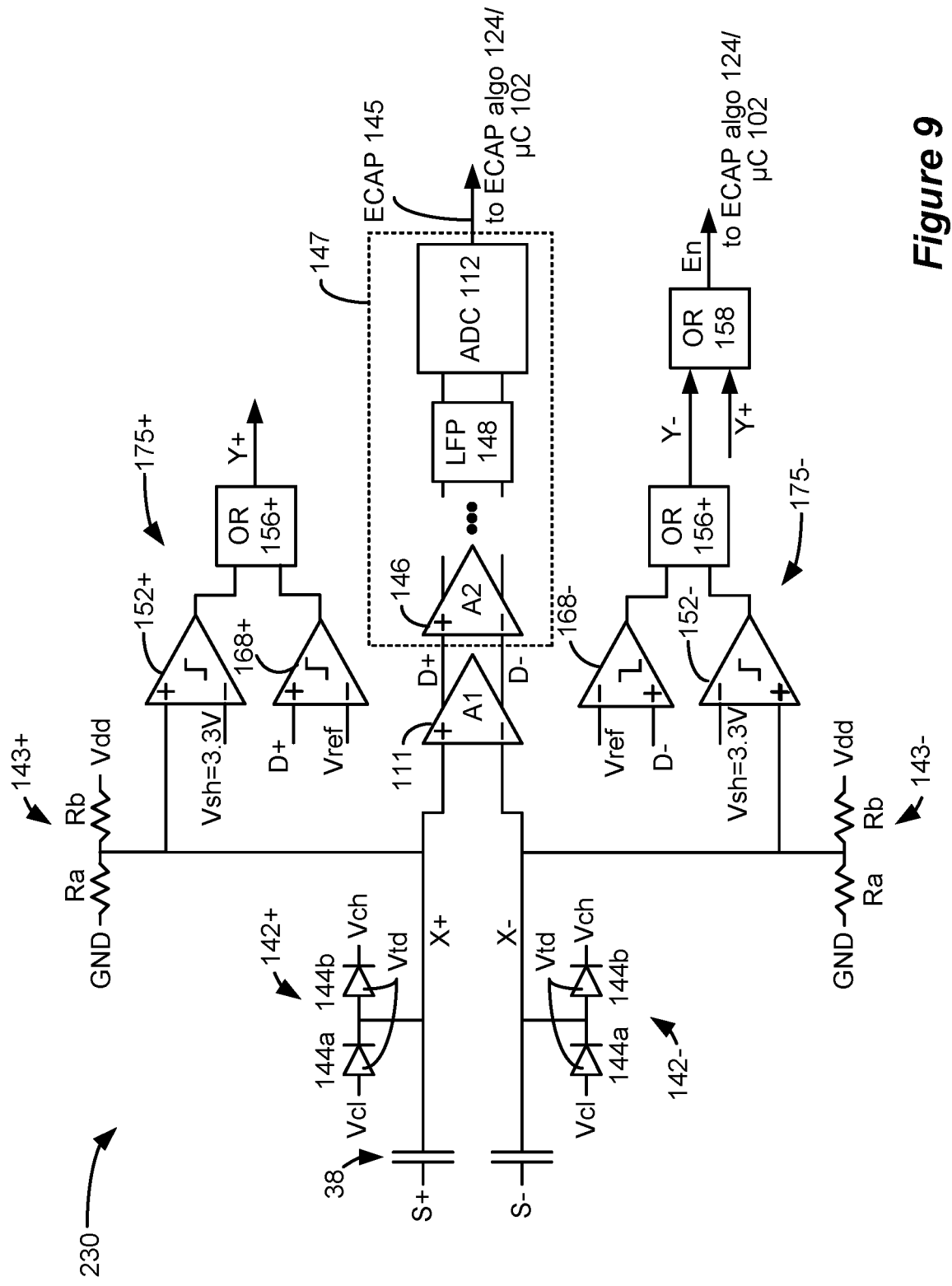
FIG. 9 shows a fourth example of a sense amp circuit combining the approaches of FIGS. 7A and 8.

The various examples of the sense amp circuits can also be combined in various ways. For example, FIG. 9 shows a sense amp circuit 230 that comprises a combination of the approaches used in sense amp circuit 210 (FIG. 7A) and sense amp circuit 220 (FIG. 8). As in circuit 220, comparators 168+ and 168− are used as part of comparator circuitries 175+ and 175−, and assess the outputs D+ and D− of the differential amplifiers 111 by comparison to Vref to inform whether inputs X+ and X− to the differential amplifier 111 are too small to turn on both of the amplifier's legs. In this respect, comparators 168+ and 168− essentially take the place of comparators 154+ and 154− in FIG. 7A. Comparators 152+ and 152− are used as before to assess inputs X+ and X− to ensure that they are not too large. The outputs of the comparators in each circuit 150+ and 150+ can again be logically ORed (156+ and 156−) to generate signals Y+ and Y−, with these signals in turn being ORed (158) to produce the enable signal, En.

When sensing tissue signals such as ECAPs, it is preferred that the sense amp circuits be used in a differential mode in which each input X+ and X− is coupleable to electrodes in contact with the patient's tissue. As noted earlier, this is desirable to try at the differential amplifier to subtract the stimulation artifact 134 as a common mode voltage, thus making it easier to sense the small-signal ECAPs.

Figure 10A:
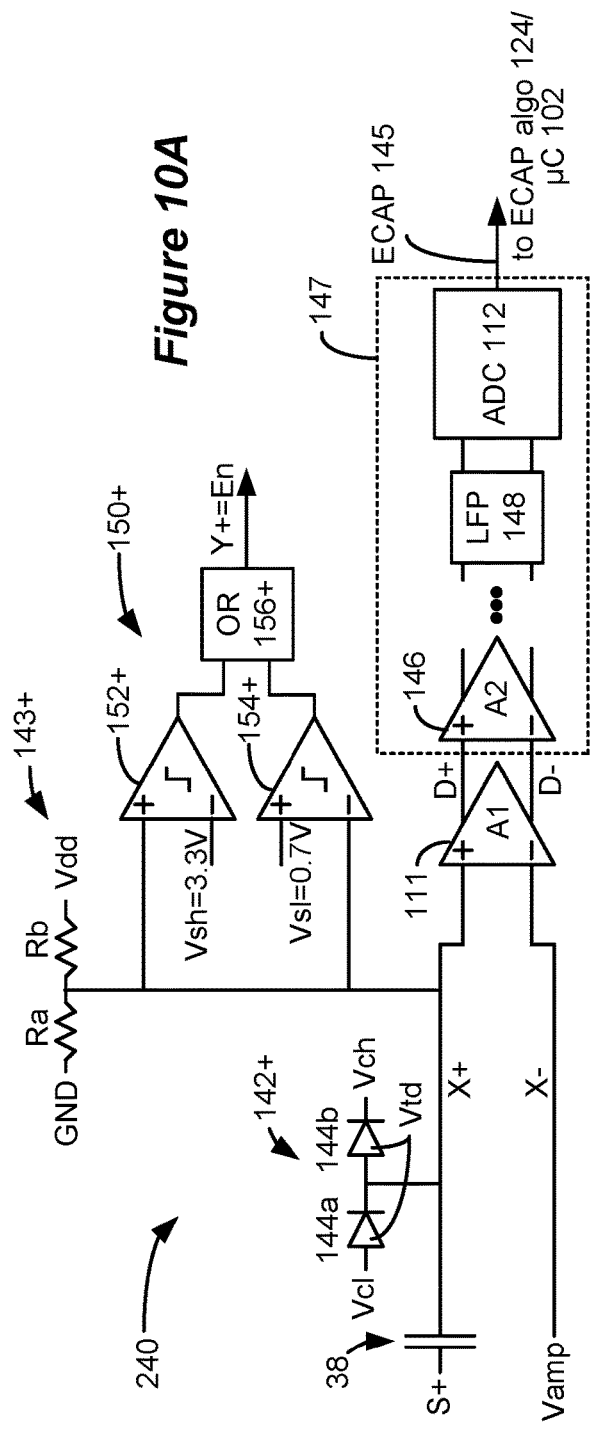
FIGS. 10A and 10B shows other examples of sense amp circuits used in a differential sensing mode, in which one of the inputs to the differential amplifier is set to a DC voltage.
Figure 10B:
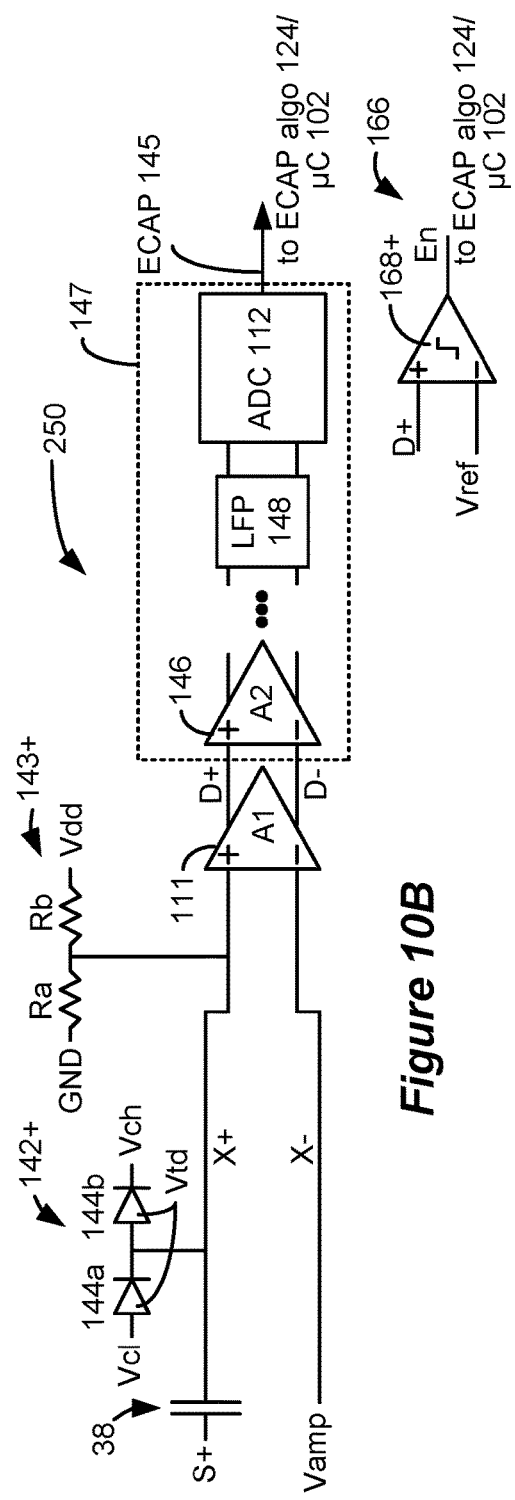

However, this is not strictly necessary, and the disclosed sense amp circuits could instead be used in a single-ended mode in which one of the amplifier inputs (e.g., X−) is set to a reference voltage, Vamp, as shown in FIGS. 10A and 10B. Such reference voltage can be a DC voltage such as ½ Vdd, 2.0 V, and should be high enough to turn on input transistor M− of the differential amplifier 111. Single-ended sensing can be useful to sense other signals at the electrodes, such as the stimulation artifact 134 itself.

FIG. 10A shows a single-ended sense amp circuit 240 which is similar to sense amp circuit 210 (FIG. 7A) shown earlier. Because X− is set to Vamp, comparator circuitry 150−, clamp circuit 142− and DC-level shifting circuit 143—are unnecessary, and thus are not shown. In reality, these circuits may still be present in sense amp circuit 240, but would simply be disabled or disconnected from the circuit when Vamp is selected (see multiplexer 108, FIG. 4) as the reference at input X−. Notice in this example that signal Y+ can operate as the enable signal that determines whether input X+ is valid, and that OR gate 158 (FIG. 4) is unnecessary.

FIG. 10B shows a single-ended sense amp circuit 250 which is similar to sense amp circuit 220 (FIG. 8) shown earlier. Because X− is set to Vamp, clamp circuit 142− and DC-level shifting circuit 143− are unnecessary, and could be disabled or disconnected. Likewise, in comparator circuitry 166, comparator 168—would be unnecessary (or disabled/disconnected), and again signal Y+ can operate as the enable signal, En.

As noted earlier, an ECAP is just one example of a neural response that can be sensed using the disclosed sense amp circuits. Not all neural responses one might desire to sense are a result of stimulation, and in this regard the disclosed sense amp circuits can be used in an implantable device that may not include stimulation circuitry 28 (FIG. 4). Furthermore, the disclosed sense amp circuits can be used to sense other types of signals in the tissue beyond neural responses. For example, the sense amp circuitry could be used to sense other types of signals, such as those used for measuring tissue field potentials or tissue resistance.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a first electrode node coupleable to a first electrode configured to make electrical contact with a patient's tissue, and a second electrode node coupleable to a second electrode configured to make electrical contact with the patient's tissue, wherein the first electrode node is configured to receive via the first electrode a tissue signal from the patient's tissue;
   an amplifier with a first input connected to the first electrode node and with a second input connected to the second electrode node, wherein the amplifier produces a first amplifier output and a second amplifier output together comprising a differential amplifier output indicative of the tissue signal;

comparator circuitry configured to
   determine from the first amplifier output a first comparator output indicating whether the first input meets an input requirement of the amplifier, and
   determine from the second amplifier output a second comparator output indicating whether the second input meets an input requirement of the amplifier; and
logic circuitry configured to receive the first comparator output and the second comparator output and to generate an enable signal, wherein the enable signal indicates whether the differential amplifier output indicative of the tissue signal is valid or invalid.

2. The implantable medical device of claim 1, wherein the first and second electrode nodes comprise two of a plurality of electrodes nodes, and wherein the first and second electrodes comprise two of a plurality of electrodes, wherein each of the plurality of electrode nodes are coupleable to a different one the plurality of electrodes, wherein the plurality of electrodes are configured to make electrical contact with the patient's tissue.

3. The implantable medical device of claim 2, further comprising a selector circuit configured to select the first and second electrode nodes from the plurality of electrode nodes.

4. The implantable medical device of claim 2, further comprising stimulation circuitry configured to produce stimulation in the tissue via selected ones of the plurality of electrodes, wherein the tissue signal is generated in the patient's tissue in response to the stimulation.

5. The implantable medical device of claim 1, wherein the second electrode comprises a conductive case of the implantable medical device.

6. The implantable medical device of claim 1, further comprising a lead, wherein the lead comprises the first and second electrodes.

7. The implantable medical device of claim 1, wherein a first blocking capacitor intervenes between the first electrode node and the first electrode, and wherein a second blocking capacitor intervenes between the second electrode node and the second electrode.

8. The implantable medical device of claim 1, wherein the tissue signal comprises a neural response.

9. The implantable medical device of claim 1, further comprising a first clamping circuit configured to keep a voltage at the first input from exceeding a first value, and a second clamping circuit configured to keep a voltage at the second input from exceeding the first value.

10. The implantable medical device of claim 9, wherein the first clamping circuit is further configured to keep the voltage at the first input from going below a second value, and wherein the second clamping circuit is further configured to keep the voltage at the second input from going below the second value.

11. The implantable medical device of claim 1, further comprising a first DC-level shifting circuit configured to set a DC voltage reference at the first input, and a second DC-level shifting circuit configured to set the DC voltage reference at the second input.

12. The implantable medical device of claim 1, wherein the amplifier comprises a first input transistor with a first control terminal for receiving the first input, and a second input transistor with a second control terminal for receiving the second input, wherein the first and second input transistors comprise a threshold voltage that must respectively be exceeded at the first and second inputs to turn on the first and second transistors.

13. The implantable medical device of claim 12, wherein the amplifier further comprises a first resistance serially connected between the first input transistor and a power supply voltage, and a second resistance serially connected between the second input transistor and the power supply voltage, wherein the first amplifier output comprises a node between the first input transistor and the first resistance, and wherein the second amplifier output comprises a node between the second input transistor and the second resistance.

14. The implantable medical device of claim 1, wherein the comparator circuitry comprises:
   a first comparator configured to indicate whether a voltage at the first differential output is below a first voltage, and
   a second comparator configured to indicate whether a voltage at the second differential output is below the first voltage.

15. The implantable medical device of claim 14, wherein the amplifier is powered by a power supply voltage, and wherein the first voltage is less than the power supply voltage.

16. The implantable medical device of claim 1, further comprising control circuitry configured to receive the differential amplifier output indicative of the tissue signal, wherein the control circuitry is programmed with an algorithm configured to analyze the amplifier output, wherein operation of the algorithm is controlled by the enable signal.

17. An implantable medical device, comprising:
   a first electrode node coupleable to a first electrode configured to make electrical contact with a patient's tissue, wherein the first electrode node is configured to receive via the first electrode a tissue signal from the patient's tissue;
   an amplifier with a first input connected to the first electrode node and with a second input connectable to a reference voltage, wherein the amplifier produces a first amplifier output and a second amplifier output together comprising a differential amplifier output indicative of the tissue signal; and
   comparator circuitry configured to determine from the first amplifier output an enable signal indicating whether the first input meets an input requirement of the amplifier, wherein the enable signal indicates whether the differential amplifier output indicative of the tissue signal is valid or invalid.

18. The implantable medical device of claim 17, further comprising stimulation circuitry configured to produce stimulation in the tissue via selected ones of the plurality of electrodes, wherein the tissue signal is generated in the patient's tissue in response to the stimulation.

19. The implantable medical device of claim 17, wherein the reference voltage comprises a DC voltage.

20. The implantable medical device of claim 17, further comprising a clamping circuit configured to keep a voltage at the first input from exceeding a first value, and a DC-level shifting circuit configured to set a DC voltage reference at the first input.

* * * * *